US011033261B2

(12) United States Patent
    Holton

(10) Patent No.: US 11,033,261 B2
(45) Date of Patent: Jun. 15, 2021

(54) SUTURE SYSTEM

(71) Applicant: Cypris Medical, Inc., Chicago, IL (US)

(72) Inventor: Daniel Holton, Evanston, IL (US)

(73) Assignee: Cypris Medical, Inc., Chicago, IL (US)

(*) Notice: Subject to any disclaimer, the term of this patent is extended or adjusted under 35 U.S.C. 154(b) by 80 days.

(21) Appl. No.: 15/994,932

(22) Filed: May 31, 2018

(65) Prior Publication Data

US 2019/0365380 A1    Dec. 5, 2019

(51) Int. Cl.
    *A61B 17/04*     (2006.01)
    *A61B 17/06*     (2006.01)
    *A61B 17/062*    (2006.01)

(52) U.S. Cl.
    CPC ...... *A61B 17/0485* (2013.01); *A61B 17/0469* (2013.01); *A61B 17/0482* (2013.01); *A61B 17/06004* (2013.01); *A61B 17/0625* (2013.01); *A61B 17/06066* (2013.01)

(58) Field of Classification Search
    CPC ............ A61B 17/0469; A61B 17/0482; A61B 2017/0404–0406; A61B 2017/048; A61B 2017/0495; A61B 17/0401; A61B 17/0483; A61B 17/0491; A61B 17/0493; A61B 2017/00269; A61B 2017/00278; A61B 2017/0408; A61B 2017/0409; A61B 2017/0472; A61B 2017/0479; A61B 2017/0496; A61F 5/0083
    See application file for complete search history.

(56) References Cited

U.S. PATENT DOCUMENTS

| | | |
|---|---|---|
| 3,206,217 A | 9/1965 | Shepard et al. |
| 4,210,148 A | 7/1980 | Stivala |
| 4,268,481 A | 5/1981 | Souvaniemi et al. |
| 4,373,530 A | 2/1983 | Kilejian |
| 4,823,794 A | 4/1989 | Pierce |
| 4,841,888 A | 6/1989 | Mills et al. |
| 4,950,283 A | 8/1990 | Dzubow et al. |
| 5,080,663 A | 1/1992 | Mills et al. |
| 5,507,754 A | 4/1996 | Green et al. |
| 5,525,302 A | 6/1996 | Astle |
| 5,549,617 A | 8/1996 | Green et al. |
| 5,562,686 A | 10/1996 | Sauer et al. |
| 5,766,186 A | 6/1998 | Faraz et al. |

(Continued)

FOREIGN PATENT DOCUMENTS

WO    2004/062466    7/2004

OTHER PUBLICATIONS

PCT International Patent Application No. PCT/US18/37406; International Search Report and Written Opinion of the International Searching Authority dated Sep. 13, 2018, 10 pages.

(Continued)

*Primary Examiner* — Elizabeth Houston
*Assistant Examiner* — Lindsey Bachman
(74) *Attorney, Agent, or Firm* — Craig R. Miles; CR Miles P.C.

(57) ABSTRACT

Generally, a suturing system including apparatus and methods for reinforcing a substrate through which a thread passes. Specifically, embodiments of a thread carrier which passes through a substrate reinforcement element adjoining a substrate to reinforce the substrate at a first location and at a second location through which the thread passes.

3 Claims, 22 Drawing Sheets

(56) References Cited

U.S. PATENT DOCUMENTS

| | | | |
|---|---|---|---|
| 5,792,153 A * | 8/1998 | Swain | A61B 17/0469 112/169 |
| 5,792,163 A | 8/1998 | Swain et al. | |
| 5,797,927 A | 8/1998 | Yoon | |
| 5,908,426 A | 6/1999 | Pierce | |
| 5,984,932 A | 11/1999 | Yoon | |
| 6,048,351 A | 4/2000 | Gordon et al. | |
| 6,059,800 A * | 5/2000 | Hart | A61B 17/0469 606/139 |
| 6,077,276 A | 6/2000 | Kontos | |
| 6,155,989 A | 12/2000 | Collins | |
| 6,346,111 B1 | 2/2002 | Gordon et al. | |
| 6,464,707 B1 | 10/2002 | Bjerken | |
| 6,533,796 B1 | 3/2003 | Sauer et al. | |
| 6,936,054 B2 | 8/2005 | Chu | |
| 6,955,643 B2 | 10/2005 | Gellman et al. | |
| 6,997,931 B2 | 2/2006 | Sauer et al. | |
| 7,033,370 B2 | 4/2006 | Gordon et al. | |
| 7,060,077 B2 | 6/2006 | Gordon et al. | |
| 7,060,079 B2 | 6/2006 | Wulc et al. | |
| 7,063,710 B2 | 6/2006 | Takamoto et al. | |
| 7,175,636 B2 | 2/2007 | Yamamoto et al. | |
| 7,220,266 B2 | 5/2007 | Gambale | |
| 7,399,304 B2 | 7/2008 | Gambale et al. | |
| 7,442,198 B2 | 10/2008 | Gellman et al. | |
| 7,517,356 B2 | 4/2009 | Heinrich | |
| 7,731,727 B2 | 1/2010 | Sauer | |
| 7,763,036 B2 | 7/2010 | Stokes et al. | |
| 7,780,684 B2 | 8/2010 | Wulc et al. | |
| 7,833,236 B2 | 11/2010 | Stokes et al. | |
| 7,846,169 B2 | 12/2010 | Shelton, IV et al. | |
| 7,951,157 B2 | 5/2011 | Gambale | |
| 8,057,386 B2 | 11/2011 | Azonian et al. | |
| 8,075,573 B2 | 12/2011 | Gambale et al. | |
| 8,100,920 B2 | 1/2012 | Gambale et al. | |
| 8,177,794 B2 | 5/2012 | Cabrera et al. | |
| 8,177,797 B2 | 5/2012 | Shimoji et al. | |
| 8,206,284 B2 | 6/2012 | Azonian et al. | |
| 8,226,665 B2 | 7/2012 | Cohen | |
| 8,246,637 B2 | 8/2012 | Viola et al. | |
| 8,257,369 B2 | 9/2012 | Gellman et al. | |
| 8,286,847 B2 | 10/2012 | Taylor | |
| 8,292,886 B2 | 10/2012 | Kerr et al. | |
| 8,292,905 B2 | 10/2012 | Taylor et al. | |
| 8,292,906 B2 | 10/2012 | Taylor et al. | |
| 8,313,509 B2 | 11/2012 | Kostrzewski | |
| 8,337,515 B2 | 12/2012 | Viola et al. | |
| 8,372,090 B2 | 2/2013 | Wingardner et al. | |
| 8,403,837 B2 | 3/2013 | Okoniewski | |
| 8,413,869 B2 | 4/2013 | Heinrich | |
| 8,465,499 B2 | 6/2013 | Onuki et al. | |
| 8,475,453 B2 | 7/2013 | Marczyk et al. | |
| 8,490,851 B2 | 7/2013 | Blier et al. | |
| 8,496,674 B2 | 7/2013 | Cabrera et al. | |
| 8,506,581 B2 | 8/2013 | Wingardner, III et al. | |
| 8,628,545 B2 | 1/2014 | Cabrera et al. | |
| 8,636,752 B2 | 1/2014 | Cabrera et al. | |
| 8,641,729 B2 | 2/2014 | Filipi et al. | |
| 8,721,640 B2 | 5/2014 | Taylor et al. | |
| 8,747,424 B2 | 6/2014 | Taylor et al. | |
| 8,882,785 B2 | 11/2014 | DiCesare et al. | |
| 8,906,041 B2 | 12/2014 | Chu | |
| 8,968,339 B2 | 3/2015 | Malkowski | |
| 8,968,340 B2 | 3/2015 | Chowaniec et al. | |
| 8,968,342 B2 | 3/2015 | Wingardner, III et al. | |
| 9,113,860 B2 | 8/2015 | Viola et al. | |
| 9,149,270 B2 | 10/2015 | Fogel | |
| 9,204,924 B2 | 12/2015 | Marczyk et al. | |
| 9,326,765 B2 | 5/2016 | Shelton, IV et al. | |
| 9,504,465 B2 | 11/2016 | Chu | |
| 10,390,818 B2 | 8/2019 | Keyser et al. | |
| 2002/0119177 A1 | 8/2002 | Bowman et al. | |
| 2003/0208209 A1 | 11/2003 | Gambale et al. | |
| 2004/0015177 A1 | 1/2004 | Chu | |
| 2004/0034371 A1 | 2/2004 | Lehman et al. | |
| 2004/0236353 A1 | 11/2004 | Bain et al. | |
| 2005/0251153 A1 * | 11/2005 | Sakamoto | A61B 17/0469 606/139 |
| 2006/0036232 A1 | 2/2006 | Primavera et al. | |
| 2006/0085016 A1 | 4/2006 | Eremia | |
| 2008/0147096 A1 | 6/2008 | Azonian et al. | |
| 2009/0018580 A1 | 1/2009 | Wulc | |
| 2010/0016868 A1 | 1/2010 | Kim | |
| 2010/0137888 A1 | 6/2010 | Wulc et al. | |
| 2010/0249498 A1 | 9/2010 | Wingardner et al. | |
| 2011/0082347 A1 | 4/2011 | Okoniewski | |
| 2012/0029536 A1 | 2/2012 | Dicesare et al. | |
| 2012/0215235 A1 | 8/2012 | Fogel | |
| 2013/0035688 A1 | 2/2013 | Kerr et al. | |
| 2013/0172685 A1 | 7/2013 | Okoniewski | |
| 2014/0012292 A1 | 1/2014 | Stewart et al. | |
| 2014/0114309 A1 | 4/2014 | Payne et al. | |
| 2014/0163375 A1 | 6/2014 | Wasielewski | |
| 2014/0371760 A1 | 12/2014 | Menn | |
| 2016/0338691 A1 | 11/2016 | Weber et al. | |

OTHER PUBLICATIONS

Covidien. SILS™ Stitch Articulating Suturing Device. Product Sheet, www.covidiet.com, originally downloaded Jan. 6, 2016, 2 pages.

Covidien. V-Loc™ Wound Closure Reload for Use With Endo Stitch™ and SILS™ Stitch Suturing Devices. Product Sheet, www.covidiet.com, originally downloaded Jan. 6, 2016, 28 pages.

Eremia et al. Novel Face-Lift Suspension Suture and Inserting Instrument: Use of Large Anchors Knotted into a Suture with Attached Needle and Inserting Device Allowing for Single Entry Point Placement of Suspension Suture. Preliminary Report of 20 Cases with 6-to 12-Month Follow-Up. Dermatol Surg., Mart 2006, 32(3):335-45.

PCT International Patent Application No. PCT/US07/21449, filed Oct. 5, 2007.

U.S. Appl. No. 60/958,474, filed Jul. 6, 2007.
U.S. Appl. No. 60/923,980, filed Apr. 17, 2007.
U.S. Appl. No. 60/923,804, filed Apr. 16, 2007.
U.S. Appl. No. 60/849,561, filed Oct. 5, 2006.
U.S. Appl. No. 60/849,508, filed Oct. 5, 2006.
U.S. Appl. No. 60/849,562, filed Oct. 5, 2006.
U.S. Appl. No. 62/473,271, filed Mar. 17, 2017.
U.S. Appl. No. 15/917,217, filed Mar. 9, 2018.

PCT International Patent Application No. PCT/US18/21942, filed Mar. 12, 2018.

PCT International Patent Application No. PCT/US18/21942; International Search Report and Written Opinion of the International Searching Authority dated May 24, 2018, 13 pages.

Non-Provisional U.S. Appl. No. 15/947,612, filed Apr. 6, 2018.

PCT International Patent Application No. PCT/US18/27173, filed Apr. 11, 2018.

U.S. Appl. No. 15/917,217; Office Action dated Sep. 8, 2019.
U.S. Appl. No. 15/947,612; Office Action dated Dec. 11, 2019.
U.S. Appl. No. 15/947,612; Office Action dated Jan. 14, 2020.
U.S. Appl. No. 16/734,121, filed Jan. 3, 2020.

PCT International Patent Application No. PCT/US18/27173; International Search Report and Written Opinion of the International Searching Authority dated Jun. 29, 2018, 8 pages.

U.S. Appl. No. 15/917,217; Office Action dated Sep. 18, 2019.
U.S. Appl. No. 15/917,217; Office Action dated Mar. 18, 2020.
U.S. Appl. No. 16/734,121, Office Action dated Feb. 2, 2021.

Boston Scientific. Capio™ Slim Suture Capturing Device. Website https://www.bostonscientific.com/capio-slim/pdf, originally downloaded Apr. 14, 2021, 4 pages.

* cited by examiner

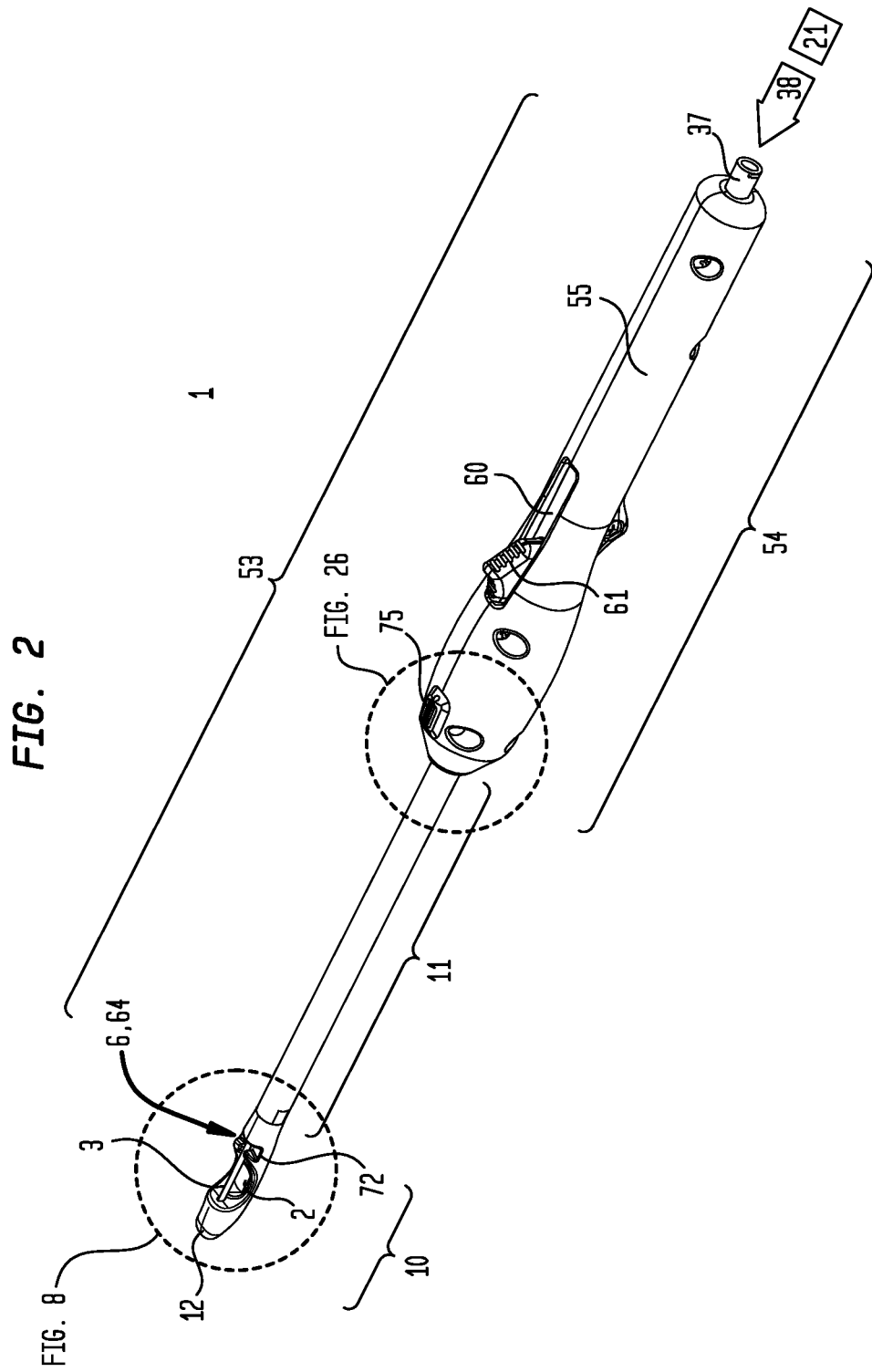

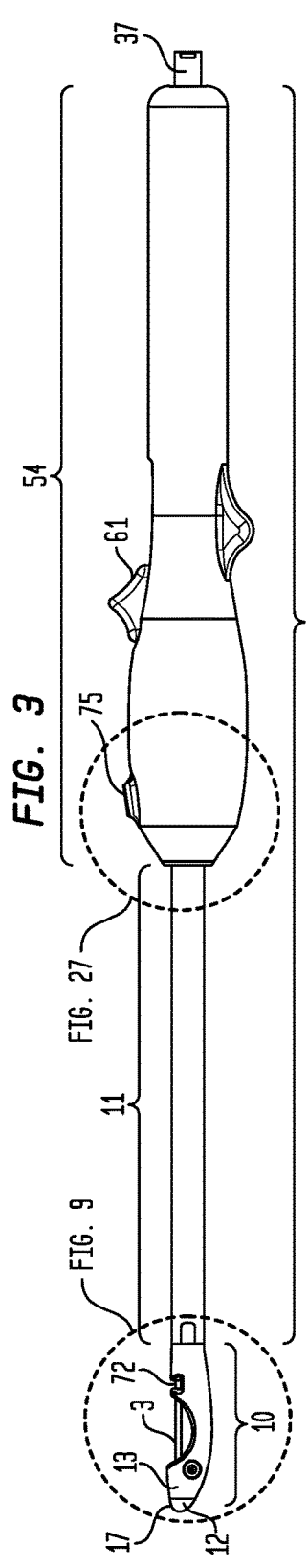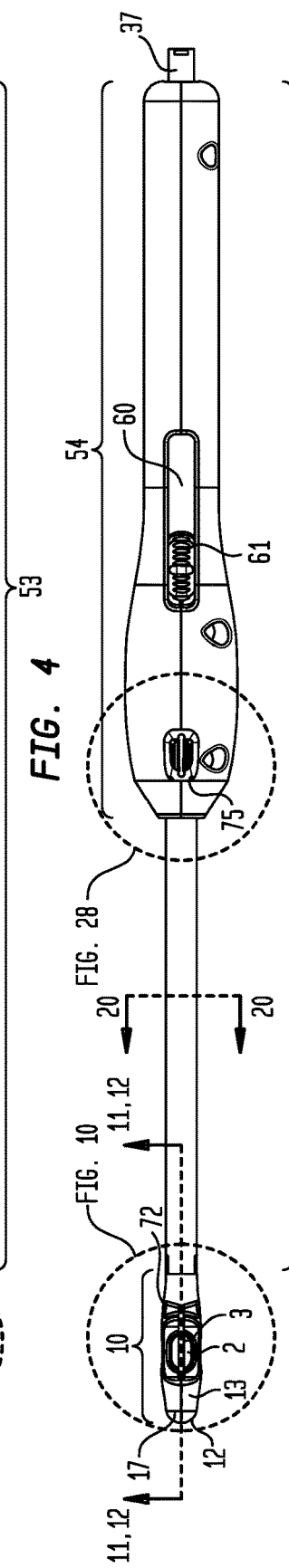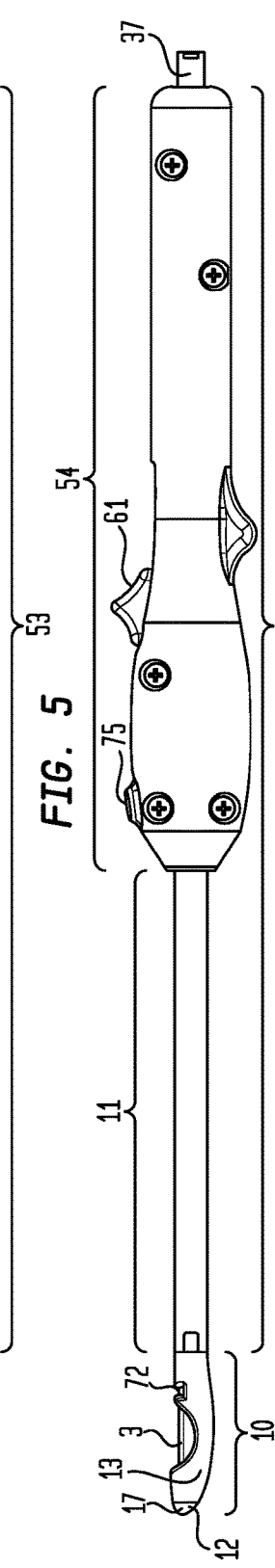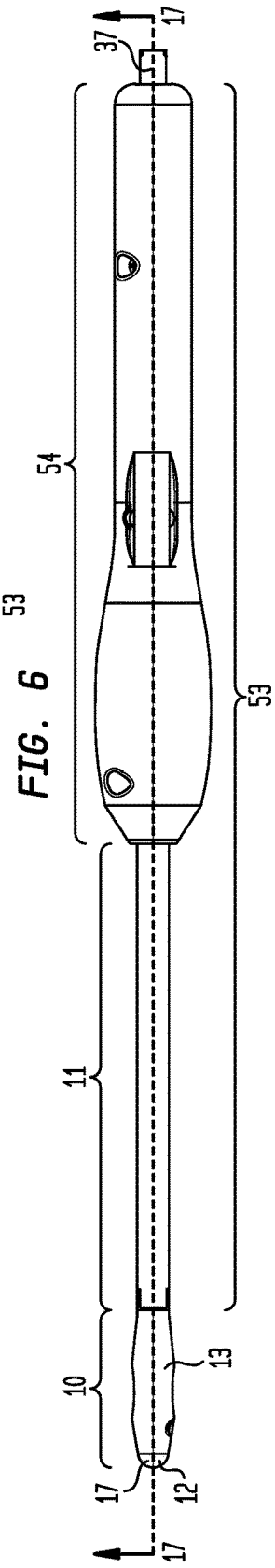

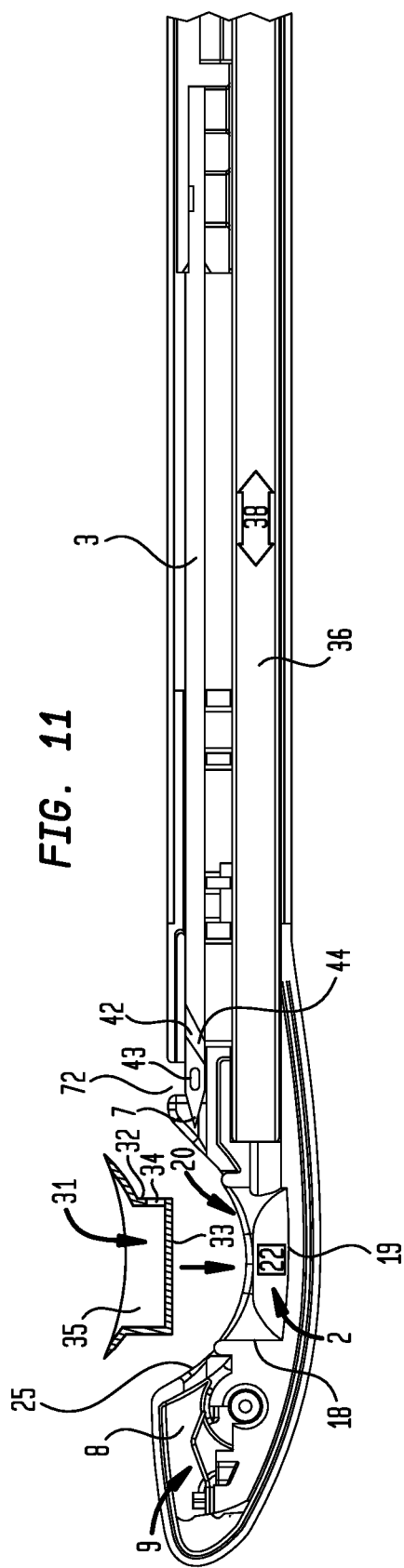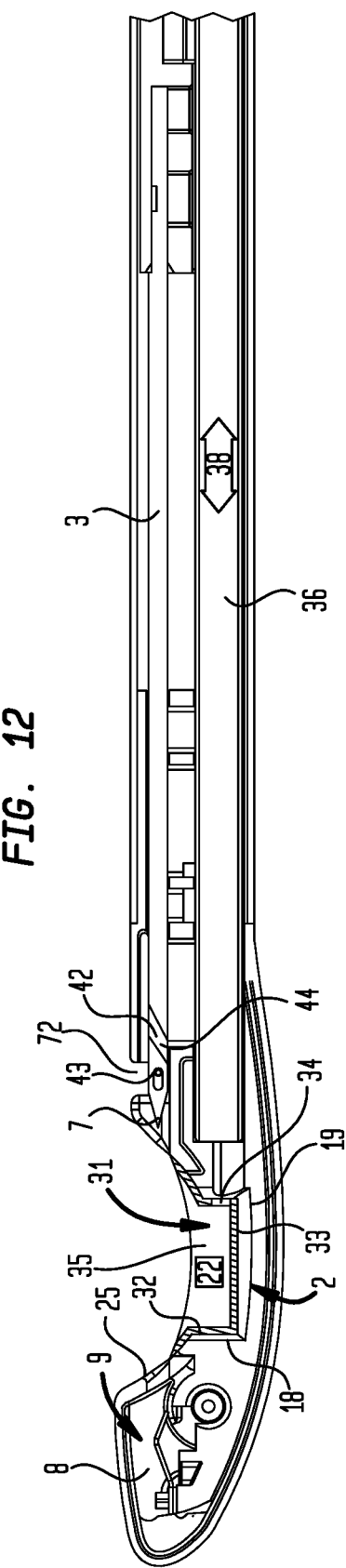

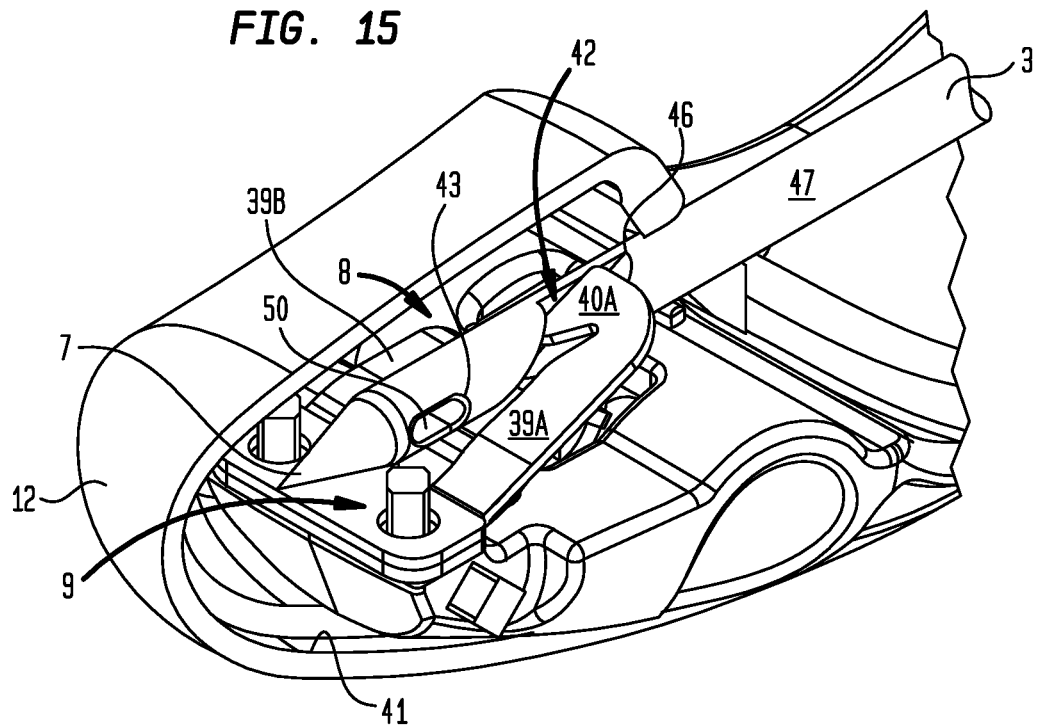
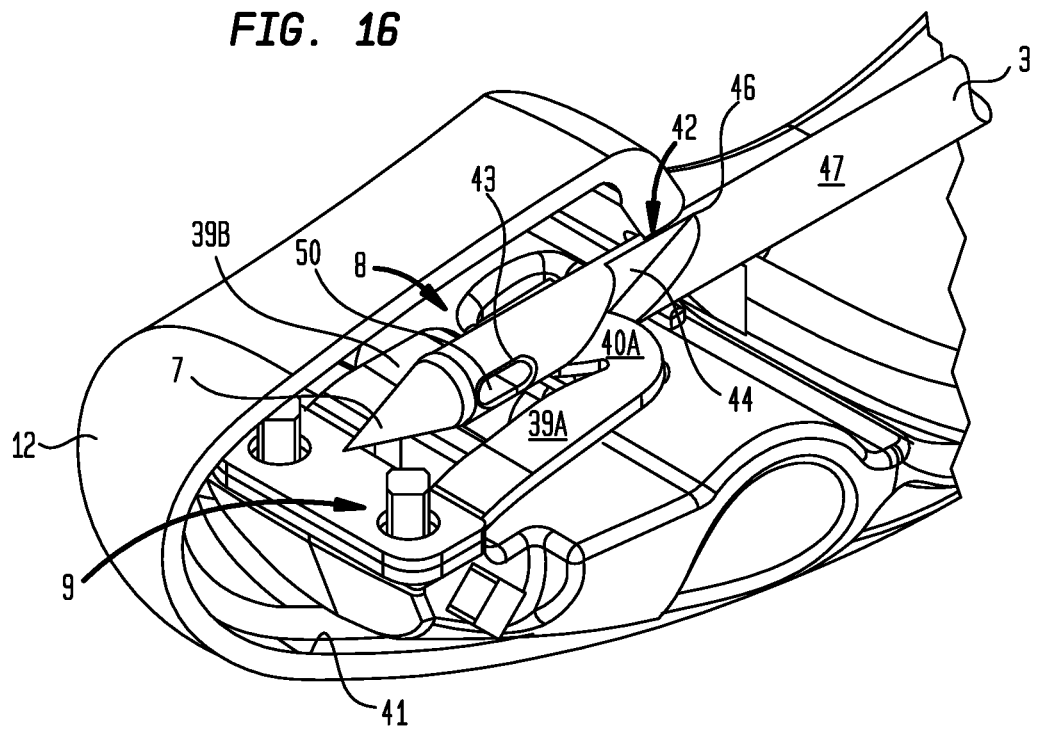

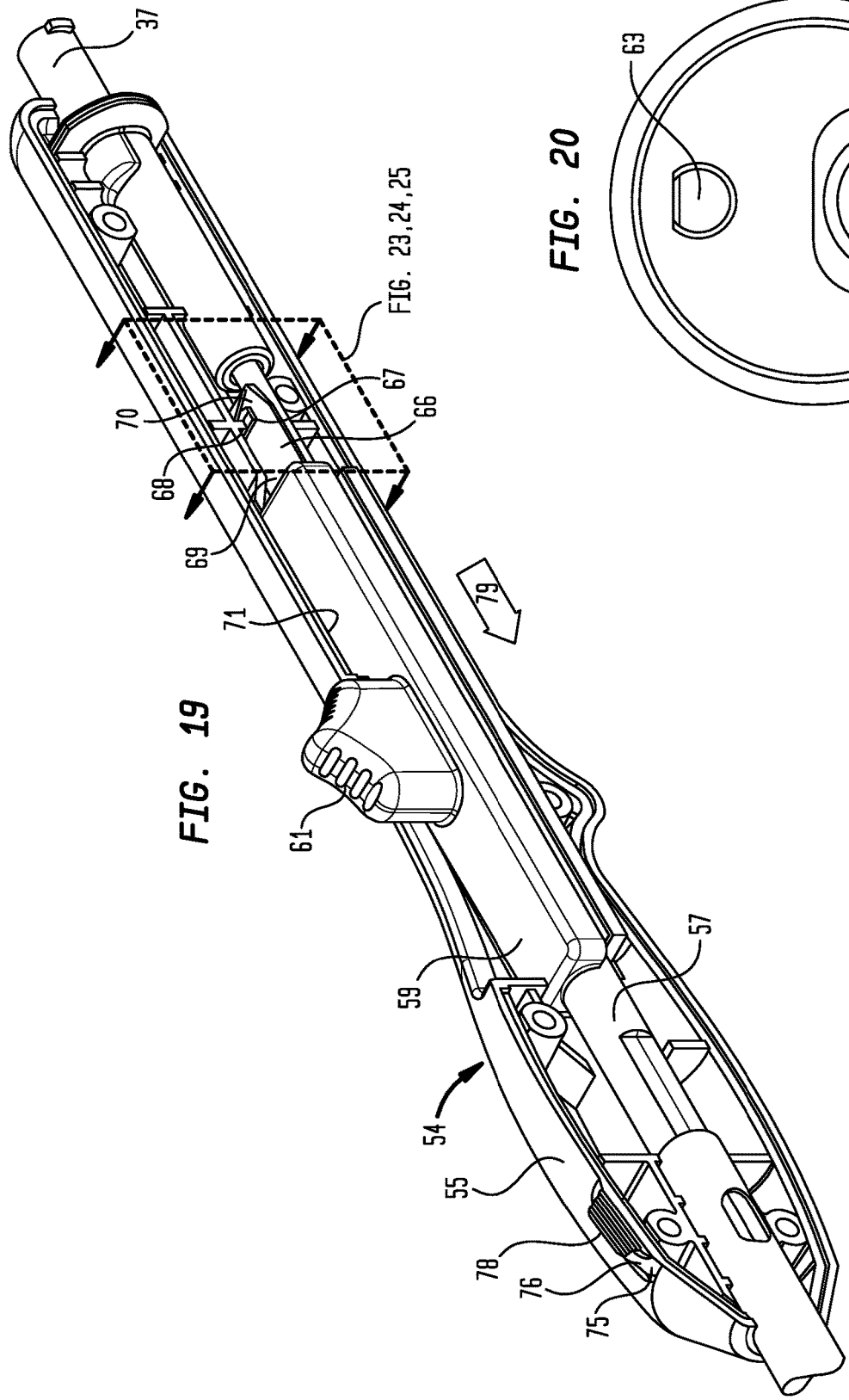
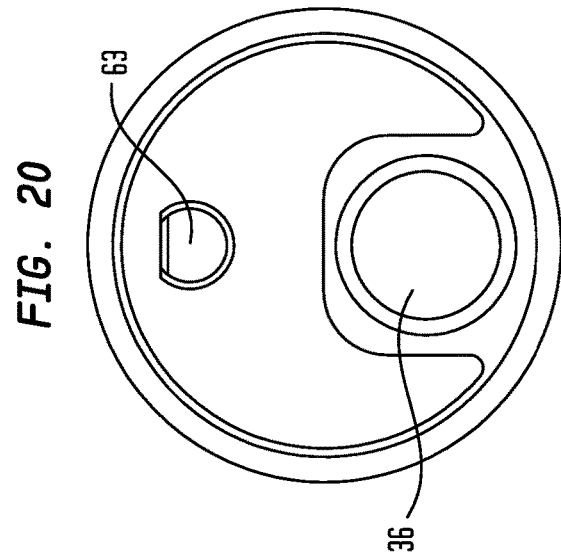

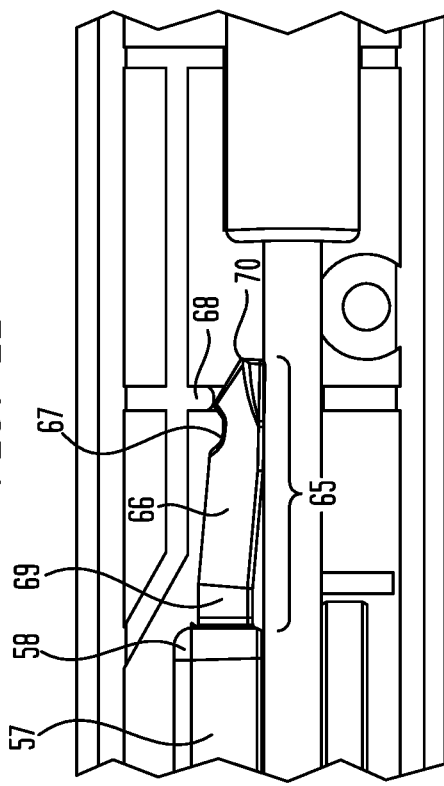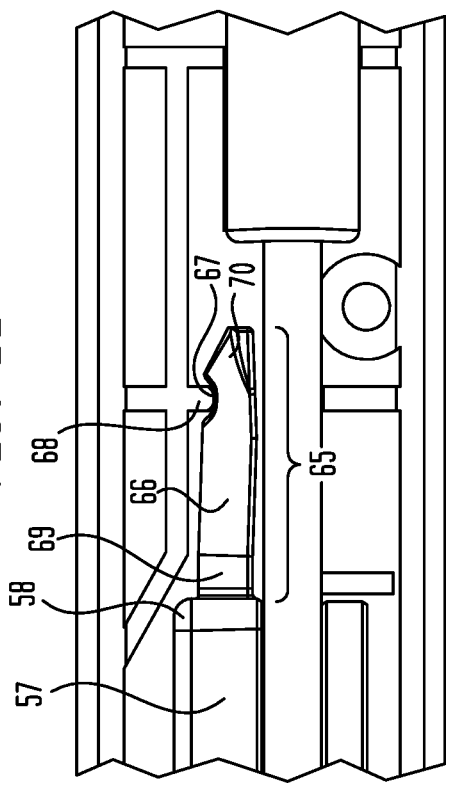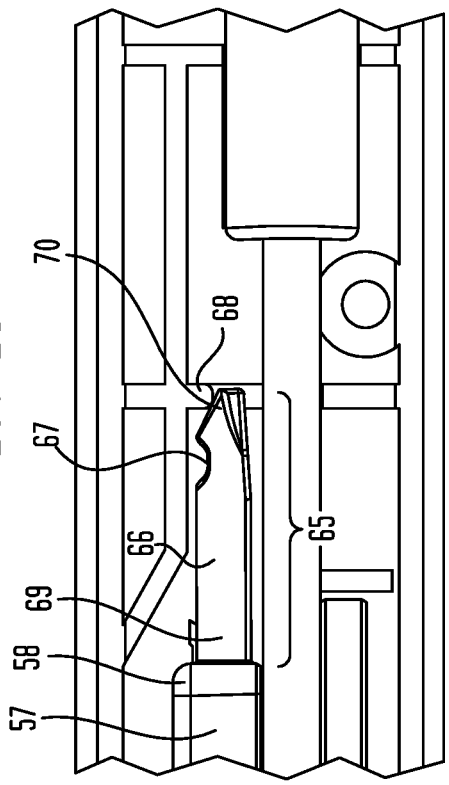

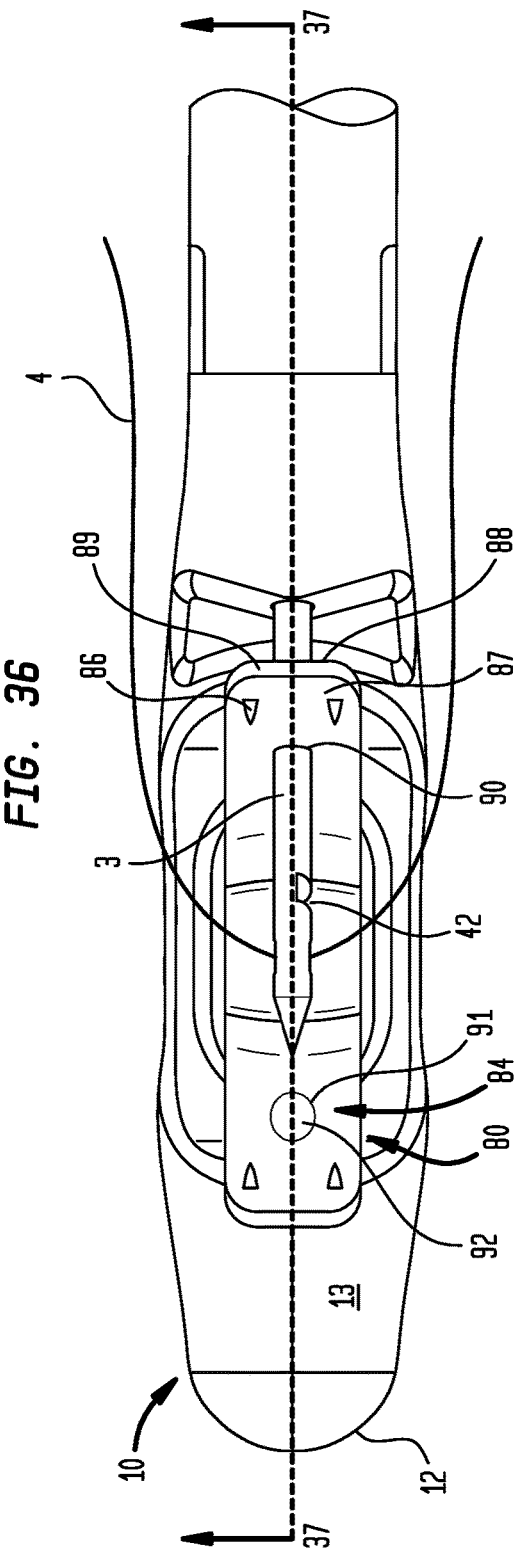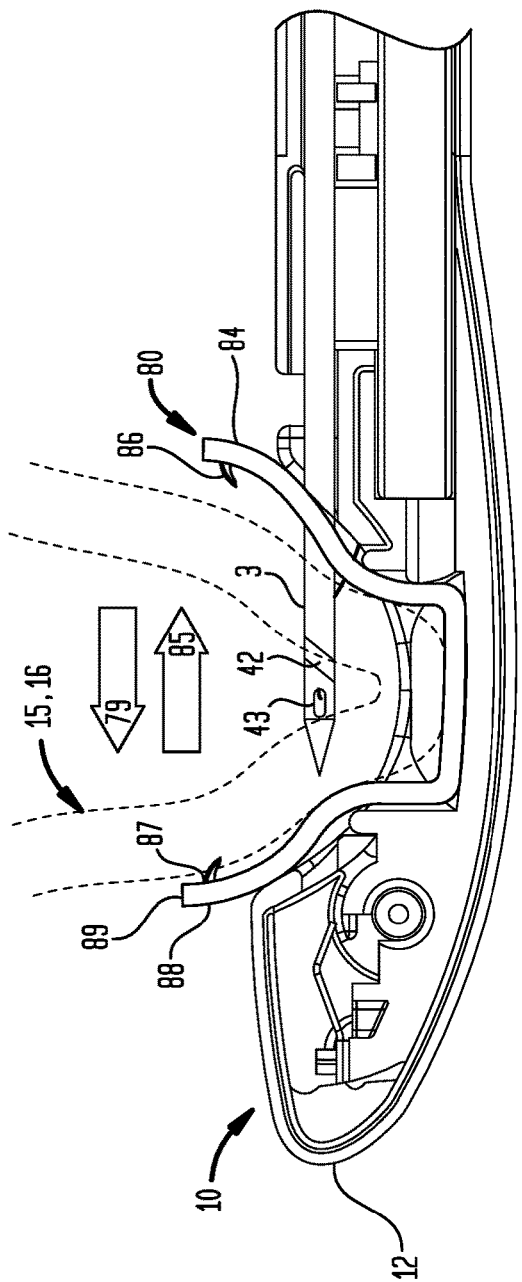

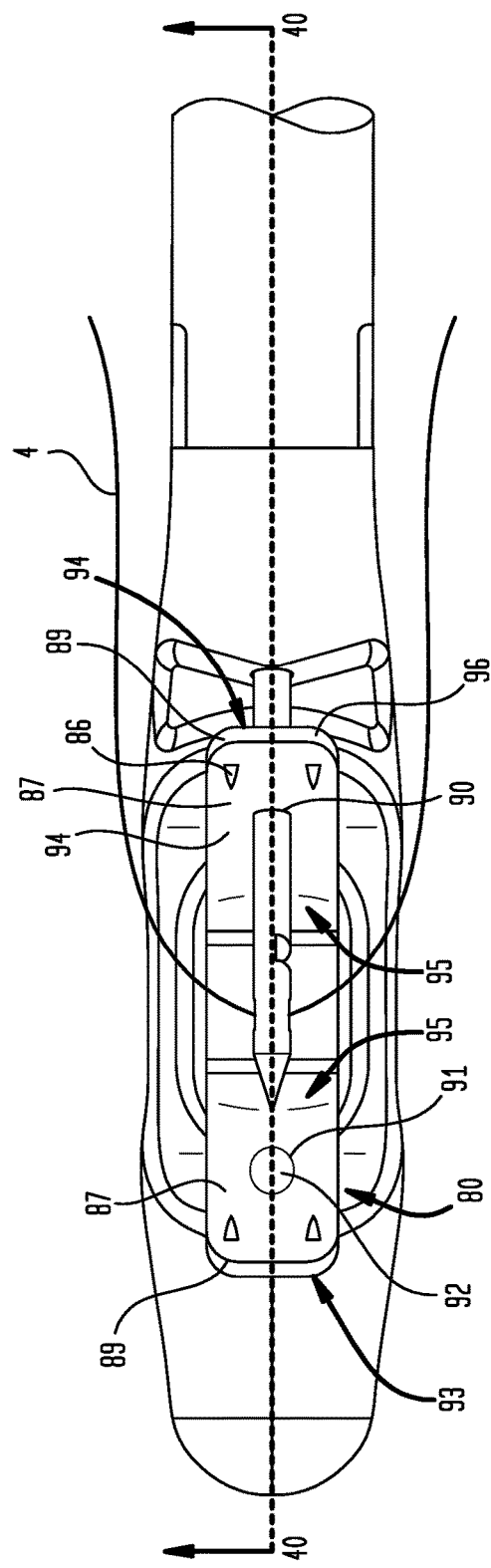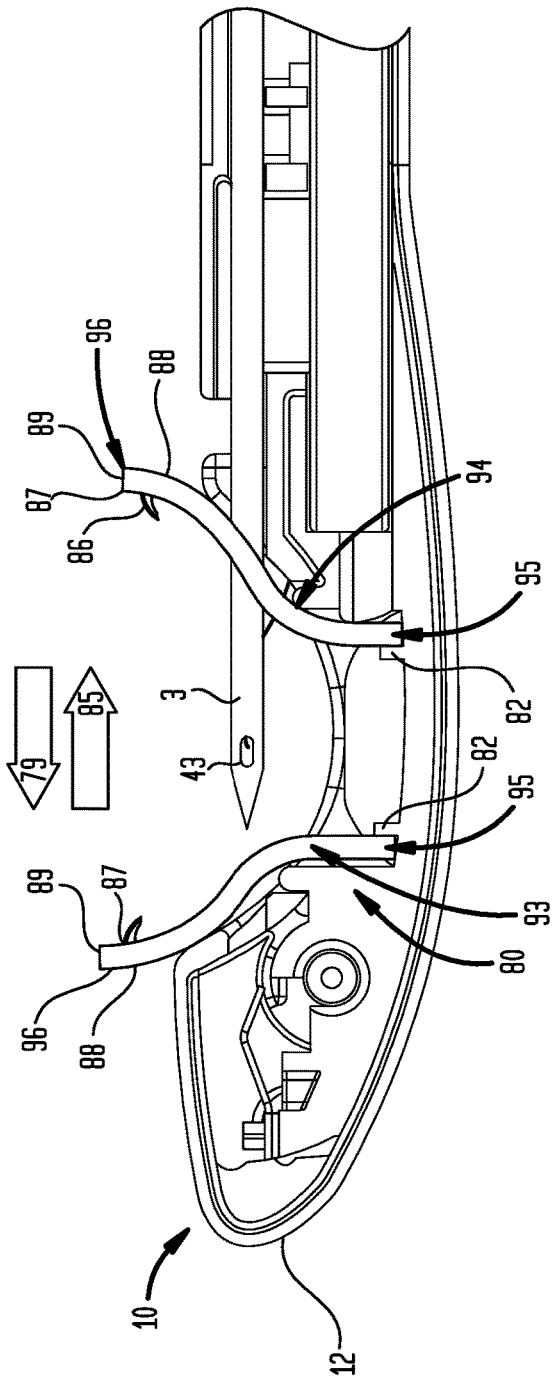

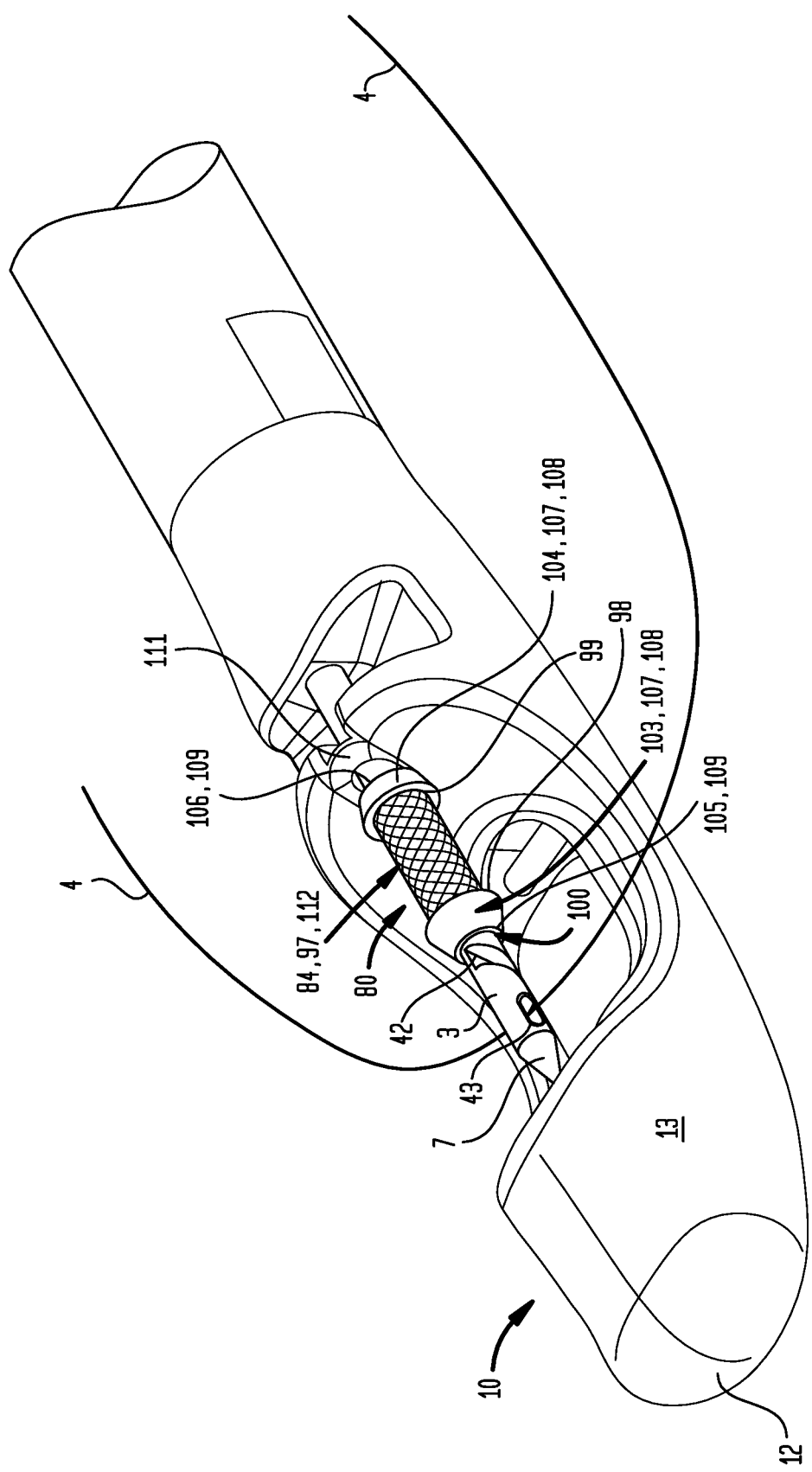

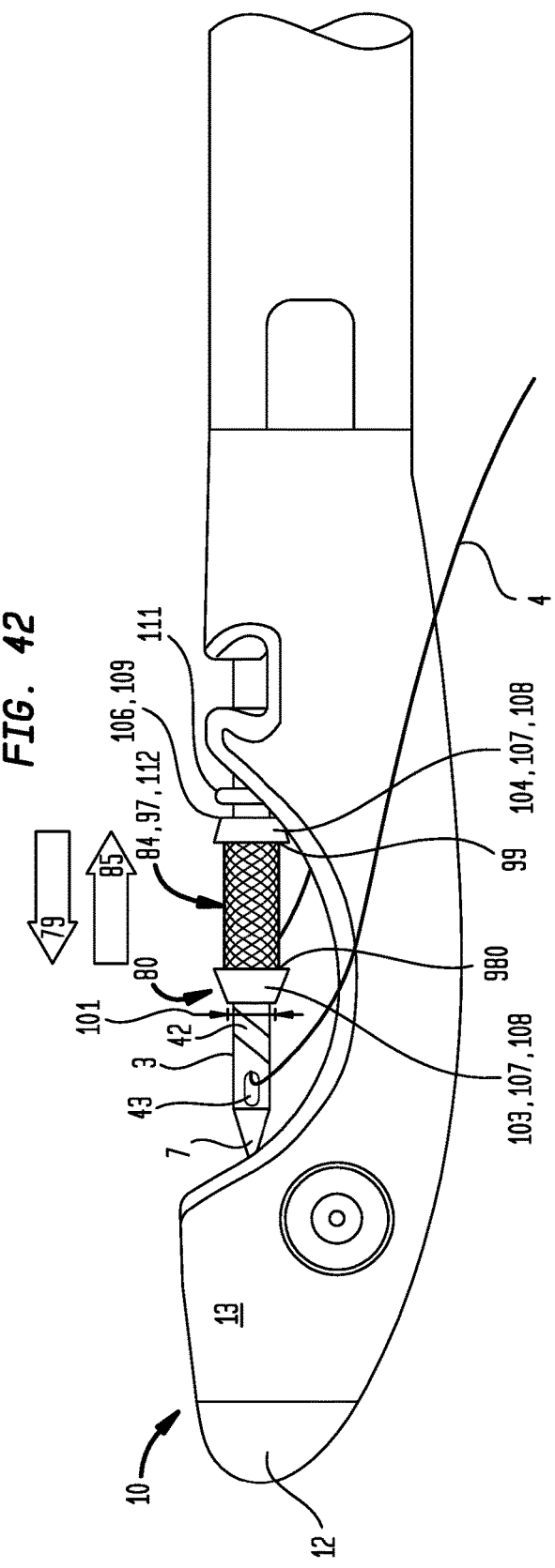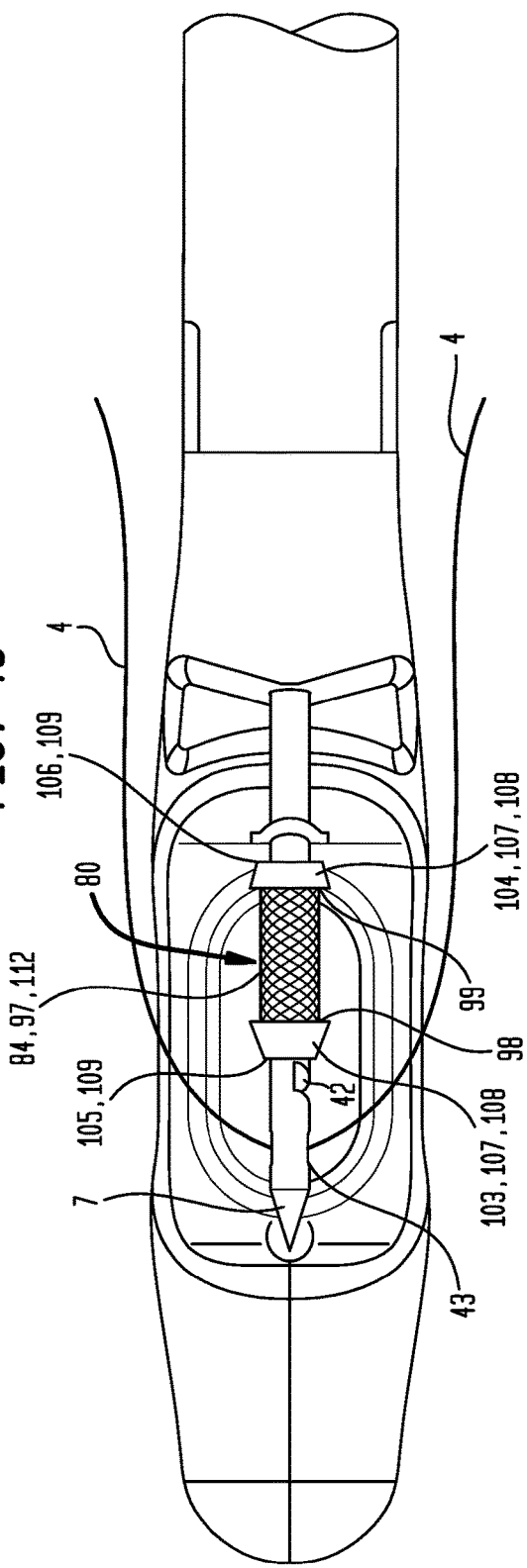

SUTURE SYSTEM

I. BACKGROUND

A suturing system including substrate reinforcement element and methods for reinforcing a thread disposed in a substrate including a thread carrier which passes through a substrate reinforcement element and an adjoining substrate to reinforce the substrate at a first location and at a second location through which the thread passes.

II. SUMMARY OF THE INVENTION

A broad object of the present invention is to provide an apparatus including one or more of a suturing probe including a thread capture chamber disposed adjacent a substrate capture chamber, a thread carrier slidingly engage to the suturing probe, and a substrate reinforcing element disposed adjacent the substrate capture chamber, where the thread carrier operably passes through the substrate reinforcing element outside of the substrate capture chamber and into the thread capture chamber.

Another broad object of the present invention is to provide a method of making an apparatus including one or more of configuring a suturing probe including disposing a thread capture chamber adjacent a substrate capture chamber, slidingly engaging a thread carrier to the suturing probe, where the thread carrier slidingly passes outside the substrate capture chamber into the thread capture chamber, and disposing a tissue reinforcing element adjacent the substrate capture chamber, where the thread carrier passes through the tissue reinforcing element.

Another broad object of the present invention is to provide a method of using an apparatus including one or more of disposing a substrate reinforcing element adjacent a substrate capture chamber of a suturing probe, capturing a substrate in the substrate capturing chamber, and driving a thread carrier slidingly engaged to the suturing probe toward a thread capture chamber disposed adjacent the substrate capture chamber, the thread carrier passing through the substrate and the substrate reinforcing element outside of the substrate capture chamber, the thread carrier passing into the thread capture chamber.

Naturally, further objects of the invention are disclosed throughout other areas of the specification, drawings, photographs, and claims.

III. A BRIEF DESCRIPTION OF THE DRAWINGS

FIG. 2 is a second perspective view of an embodiment of the suturing apparatus having the thread carrier in an extended condition.

FIG. 3 is a first side elevation view of an embodiment of the suturing apparatus.

FIG. 4 is a top plan view of an embodiment of the suturing apparatus.

FIG. 5 is a second side elevation view of an embodiment of the suturing apparatus.

FIG. 6 is a bottom plan view of an embodiment of the suturing apparatus.

FIG. 11 is a cross section view 11-11 as shown in FIG. 4 which depicts an embodiment of the suturing probe further including a substrate capture chamber which removably inserts into a substrate capture chamber.

FIG. 12 is a cross section view 12-12 as shown in FIG. 4 which depicts an embodiment of the suturing probe having the substrate capture chamber inserted into the substrate capture chamber.

FIG. 15 is an enlarged view of a particular embodiment of a thread carrier and a thread capture chamber showing the position of the thread carrier extended a distance into the thread capture chamber to align a hook of the thread capture assembly with a notch in the thread carrier.

FIG. 16 is an enlarged view of a particular embodiment of a thread carrier and a thread capture chamber showing the position of the thread carrier slidingly withdrawn from the thread capture assembly to allow the hook to pass through the notch in the thread carrier.

FIG. 19 is an enlarged perspective view of a portion of the cross section of the suturing apparatus handle shown in FIG. 17.

FIG. 20 is an enlarged view of cross section 20-20 of a tubular member of the suturing apparatus shown in FIG. 4.

FIG. 21 is an enlarged cross section view of an arrest assembly of the suturing apparatus in a thread carrier first position.

FIG. 22 is an enlarged cross section view of an arrest assembly of the suturing apparatus between a thread carrier first position and a thread carrier second position.

FIG. 23 is an enlarged cross section view of an arrest assembly of the suturing apparatus in a thread carrier second position.

FIG. 36 is a top plan view of an embodiment of a suturing apparatus including a particular embodiment of a substrate reinforcing element.

FIG. 37 is a cross section view 37-37 of the suturing apparatus shown in FIG. 36.

FIG. 39 is a top plan view of an embodiment of a suturing apparatus including another particular embodiment of a substrate reinforcing element.

FIG. 40 is a cross section view 40-40 as shown in FIG. 39.

FIG. 41 is a perspective view of an embodiment of a suturing apparatus including another particular embodiment of a substrate reinforcing element.

FIG. 42 is a side view of an embodiment of a suturing apparatus including another particular embodiment of a substrate reinforcing element.

FIG. 43 is a top plan view of an embodiment of a suturing apparatus including another particular embodiment of a substrate reinforcing element.

IV. DETAILED DESCRIPTION OF THE PREFERRED EMBODIMENTS

Figure 1:
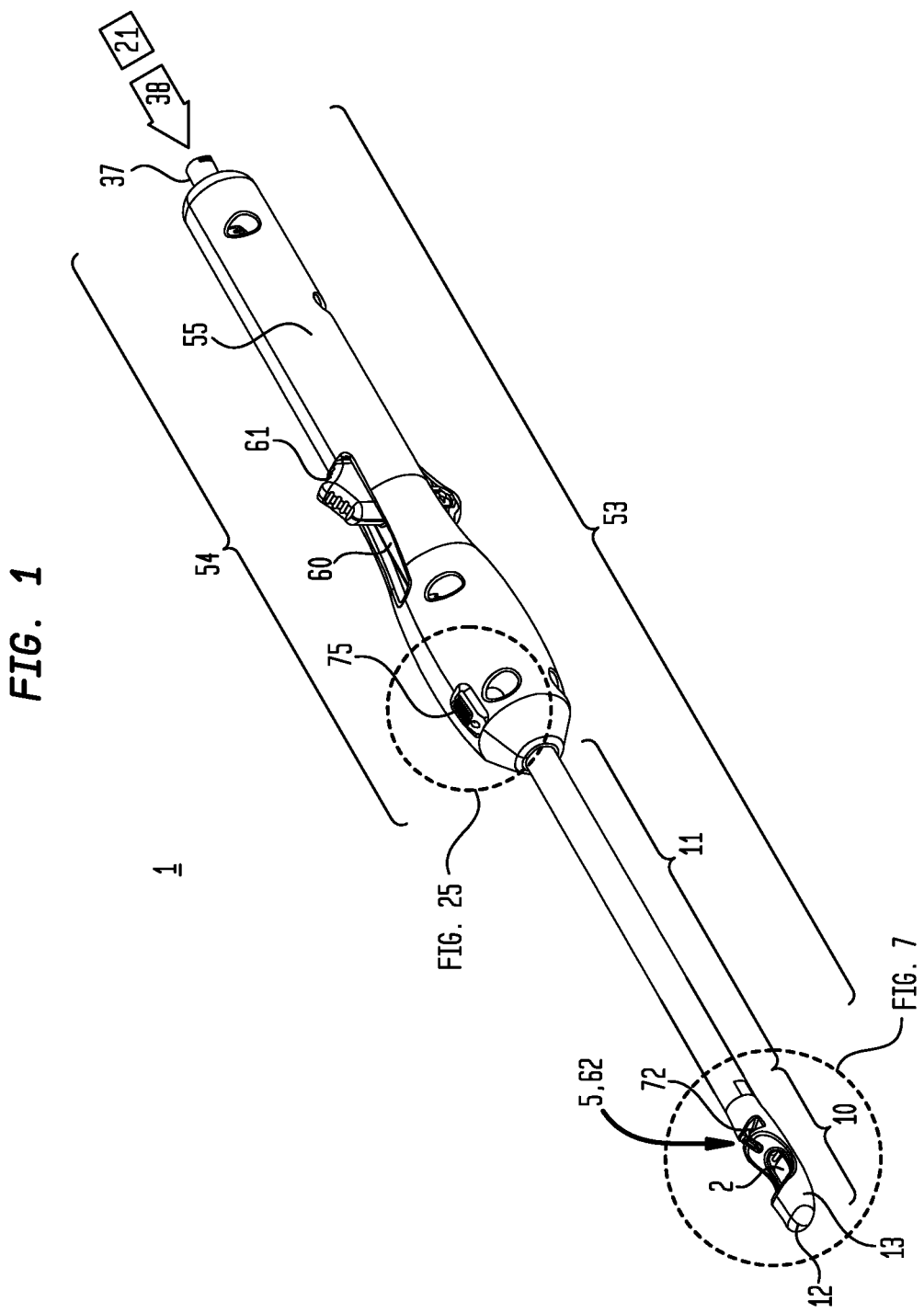
FIG. 1 is a first perspective view of an embodiment of the suturing apparatus having a thread carrier in a retracted condition.
Figure 8:
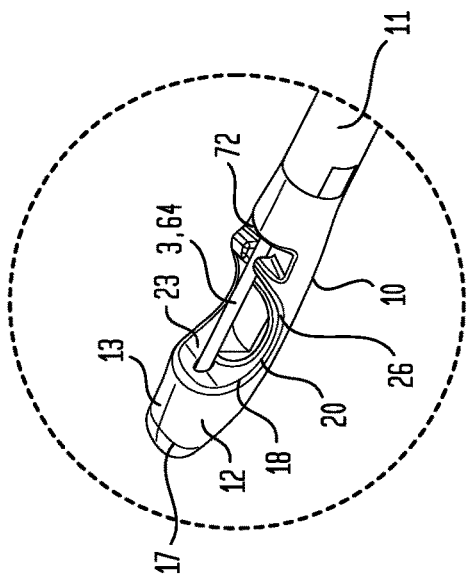
FIG. 8 is an enlarged view of the suturing probe shown FIG. 2.
Figure 10:
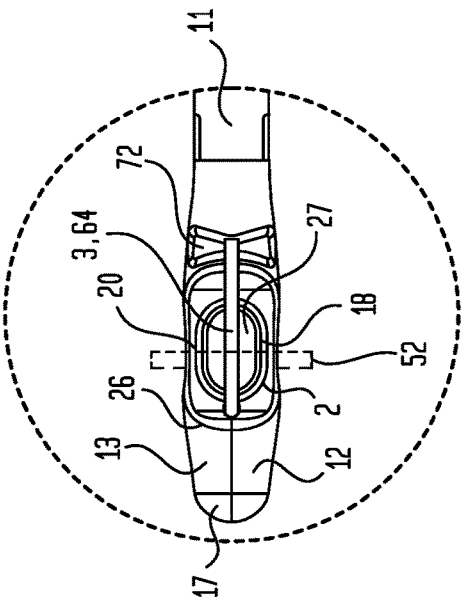
FIG. 10 is an enlarged view of the suturing probe shown in FIG. 4.

Generally referring to FIGS. 1 through 43, embodiments of a suturing apparatus (1) including a substrate capture chamber (2) and a thread carrier (3) carrying a thread (4) which axially moves between a retracted condition (5) toward an extended condition (6) in which a thread carrier terminal end (7) of the thread carrier (3) passes outside of the substrate capture chamber (2) into a thread capture chamber (8) to engage a thread capture assembly (9) which captures the thread (4) to generate a thread loop upon return of the thread carrier (3) toward the retracted condition (5).

Now referring primarily to FIGS. 1 through 10, embodiments of the suturing apparatus (1) can include a suturing probe (10). The suturing probe (10) can outward axially extend from a tubular member (11) to terminate in a probe tip (12). The suturing probe external surface (13) can, but need not necessarily, be configured as an extension of the external dimensions of the tubular member (11) allowing the probe tip (12) to pass through body openings (14) such as natural body openings or incisions to engage a substrate (15) (as shown in the illustrative example of FIGS. 33A through 33E) such as skin, fascia, fat, or muscle. While particular examples of a substrate (15) include tissue (16) including human or animal tissue, this description is not intended to preclude the capture of substrates (15) other than human or animal tissue, including as illustrative examples, cadaver tissue, simulants of tissue, tissue models, elastomer components, plastic or natural fabrics, or the like.

Again, referring primarily to FIGS. 1 through 10, in particular embodiments, the suturing probe (10) can have a generally cylindrical suturing probe external surface (13) terminating in a hebetated probe tip (12). As to particular embodiments, the suturing probe external surface (13) can include a tapered, beveled, or sloped surface approaching the probe tip (12) to reduce dimensions at the probe tip (12). There can be an advantage in having a sloped, tapered or inclined probe face (17) as it allows the suturing probe (10) additional ingress into a substrate (15) such as animal tissues with a lesser amount of tissue dissection or trauma.

Again, referring primarily to FIGS. 1 through 10, in particular embodiments, a substrate capture chamber (2) can be disposed in the suturing probe (10). The substrate capture chamber (2) can include a chamber sidewall (18) which couples in opposed fixed relation a chamber bottom (19) a distance from said chamber port (20) open to the suturing probe external surface (13). In particular embodiments, the vertical chamber side wall (18) can define a periphery of greater circumference than the periphery of the chamber port (20). In particular embodiments, the substrate capture chamber (2) can, but need not necessarily, be fluidically coupled to a vacuum source (21) operable to generate a reduced chamber pressure (22) in the substrate capture chamber (2) sufficient to capture, draw, or dispose a substrate (15) into the substrate capture chamber (2).

In particular embodiments, the suturing probe (10) can include a recessed portion (23) with the chamber port (20) open to the recessed portion (23) of the suturing probe external surface (13) with the thread carrier (3) operable to pass within the recessed portion (23) of the suturing probe external surface (13) outside of the substrate capture chamber (2). In particular embodiments, the recessed portion (23) of the suturing probe external surface (13) can be arcuate (as shown in the illustrative examples of FIGS. 7 through 9). The arcuate recessed portion (23) of the suturing probe external surface (13) can, but need not necessarily, be configured to allow a tip of a finger (24) to apply force to a substrate (15) to move the substrate toward the substrate capture chamber (2) (as shown in the illustrative example of FIG. 33C).

Now referring primarily to FIGS. 7 through 10, the recessed portion (23) of the suturing probe external surface (13) can include a substantially flat arcuate face (25) in which the chamber port (20) opens to provide a recessed peripheral margin (26) about the chamber port (20). There can be an advantage in a recessed peripheral margin (26) which affords a substantially flat or lessened curvature about the chamber port (20) in that it can increase the surface area of the suturing probe external surface (13) contacting a substrate (15). The increased surface area of the suturing probe external surface (13) can afford a substantial advantage in capture of a substrate (15) in those embodiments in which a reduced chamber pressure (22) can be generated in the substrate capture chamber (2) or can decrease movement of the suturing probe (10) in relation to the substrate (15) captured in the substrate capture chamber (2).

Now referring primarily to FIGS. 1, 2, 4, and 10, the chamber port (20) can, but need not necessarily, be disposed in a stadium configuration (27), being a rectangle with semicircles at a pair of opposite sides. The substrate capture chamber (2) can, but need not necessarily, have a chamber bottom (19) in a stadium configuration disposed opposite the chamber port (20) in stadium configuration connected by a substantially vertical chamber sidewall (18).

Figure 34:
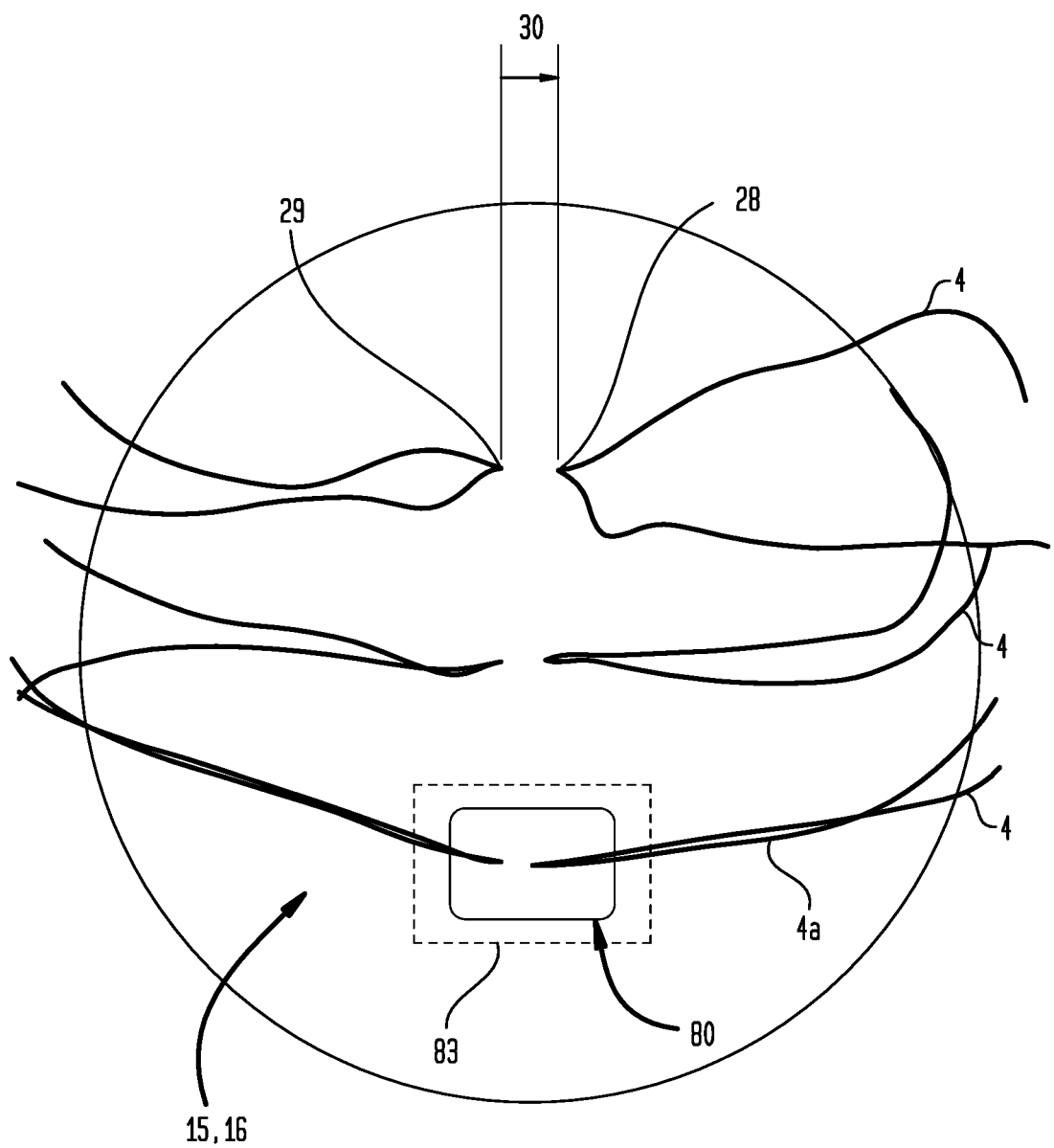
FIG. 34 is an illustration of different amounts of substrate purchase obtained by use of different configurations of the suturing apparatus and an embodiment of a substrate reinforcing element sutured adjacent the substrate.

Referring to FIG. 34, there can be an advantage in a substrate capture chamber (2) of stadium configuration (27) in that an increased amount of substrate (15) can be disposed in the substrate capture chamber (2) as compared to a substrate capture chamber (2) having conventionally slotted or substantially circular substrate capture chamber (2) and correspondingly the substrate (15) penetrated by the thread carrier (3) can dispose a thread entry point (28) and a thread withdraw point (29) a greater distance apart (also referred to as the "suture purchase (30)") as compared to conventional slotted or cylindrical suction chambers. The suture purchase (30) generated by use of a stadium configuration (27) can be substantially greater than that obtained using a suction chamber of cylindrical configuration or obtained using a conventional suction chamber of slotted configuration. It may be that the conventional cylindrical configuration draws the substrate into a conical configuration within the conventional cylindrical suction chamber and the conventional needle only penetrates the substrate proximate the apex of the cone. It may be that the conventional slotted suction chamber does not have sufficient volume to dispose the substrate a sufficient distance into the conventional slotted chamber and the conventional needle only penetrates the substrate layers in adjacent relation close to the fold or edges.

Now referring to FIGS. 11 and 12, particular embodiments of the suturing probe can include a substrate capture chamber insert (31). The substrate capture chamber insert (31) can include a substrate capture chamber insert sidewall (32) which joins a substrate capture insert bottom (33) to a substrate capture chamber insert port (34). The substrate capture chamber insert (31) can be removably coupled to the inside of the substrate capture chamber (2) to alter the configuration or volume of the substrate capture chamber (2). The altered configuration or volume corresponding to the substrate capture chamber insert (31) can accordingly increase or decrease the volume of substrate (15) captured in the substrate capture chamber (2) and accordingly adjust the suture purchase (30) (as shown in the illustrative example of FIG. 34). The substrate capture chamber insert (31) can have an insert aperture element (35) disposed to fluidically couple the internal volume of the substrate capture chamber insert (31) and substrate capture chamber insert port (34) with a first longitudinal channel (36) which couples the substrate capture chamber (2) to a vacuum port (37) through which fluid flow (38) passes to regulate the chamber pressure (22) within the substrate capture chamber (2). As shown in the illustrative example of FIG. 12, the substrate capture chamber insert (31) can have a substrate capture chamber insert bottom (33) which between interchangeable embodiments can be disposed at a depth equal to or less than the distance between the substrate capture chamber bottom (19) and the chamber port (20). The substrate capture chamber insert port (34) can have an open area about equal to or less than the open area defined by the chamber port (20). However, this illustrative example is not intended to preclude other configurations of the substrate capture insert (31) which can alter only the chamber sidewall (18), only the chamber port (20), or only the chamber bottom (19), or combinations thereof.

Figure 13:
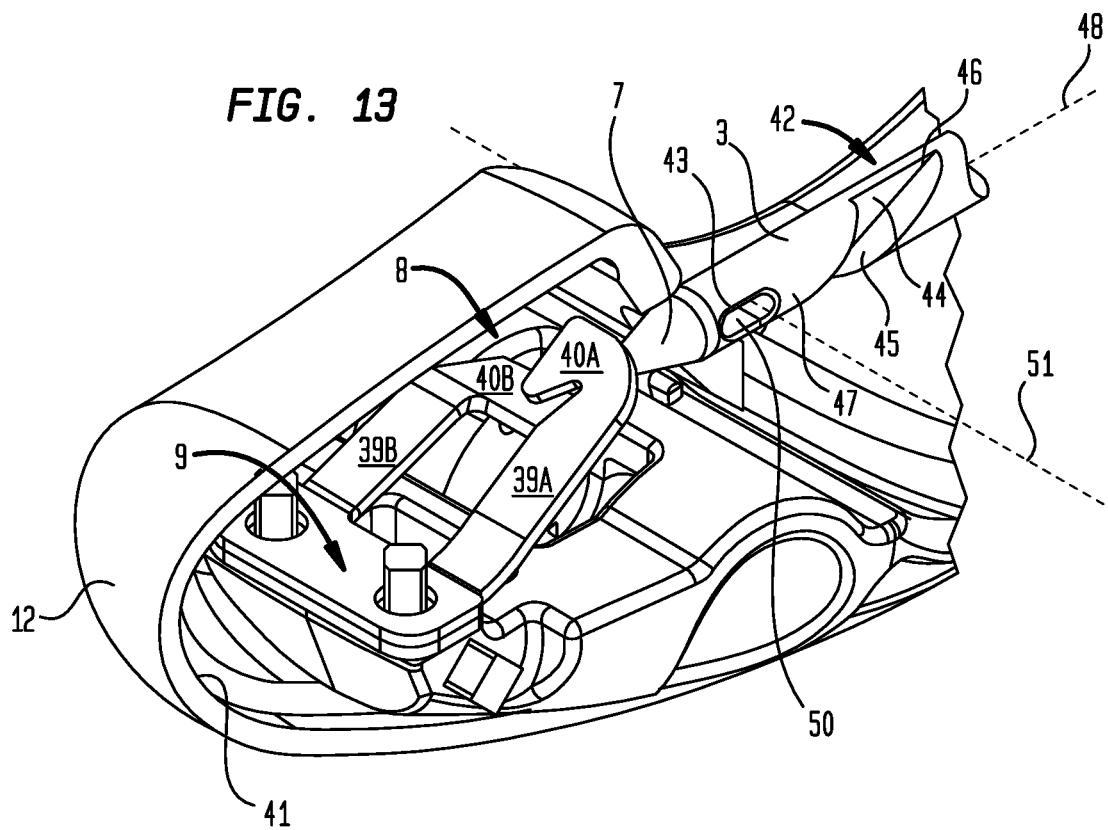
FIG. 13 is an enlarged view of a particular embodiment of a thread carrier and a thread capture chamber showing the position of the thread carrier extended a distance into the thread capture chamber.
Figure 14:
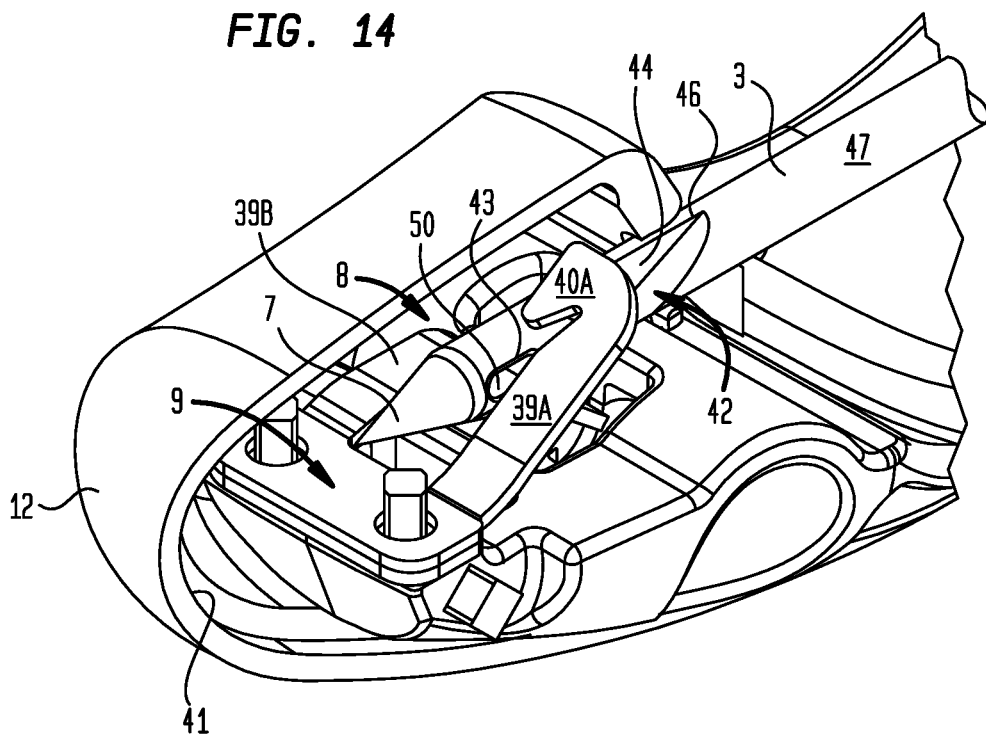
FIG. 14 is an enlarged view of a particular embodiment of a thread carrier and a thread capture chamber showing the position of the thread carrier extended a distance into the thread capture chamber to slidingly engage a thread capture assembly.

Now referring primarily to FIGS. 13 through 16, a thread capture assembly (9) can be disposed in the thread capture chamber (8). The thread capture assembly (9) can include at least one resiliently flexible hook member (39A) correspondingly terminating in at least one hook (40A). The resiliently flexible hook member (39A) can be coupled to the thread capture chamber internal surface (41) to dispose the hook (40A) at a location to engage the thread carrier (3) and flexing the at least one resiliently flexible hook member (39A). As to particular embodiments, the thread capture assembly (9) can include a pair of resiliently flexible hook members (39A)(39B) each correspondingly terminating in one of a pair of hooks (40A)(40B). The pair of resiliently flexible hook members (39A)(39B) can each be coupled to the thread capture chamber internal surface (41) to dispose the pair of hooks (40A)(40B) a distance apart at locations which allow corresponding engagement on opposed sides of the thread carrier (3), thereby flexing each of the pair of resiliently flexible hook members (39A)(39B) (as shown in the example of FIGS. 13 and 14). Upon retraction of the thread carrier (3) from the thread capture chamber (8), the pair of resiliently flexible hook members (39A)(39B) each return toward the unflexed condition correspondingly disengaging each of the pair of hooks (40A)(40B) from the thread carrier (3).

Again, referring primarily to FIGS. 13 through 16, the thread carrier (3) can further include a notch (42) disposed a distance axially from the thread carrier aperture element (43). The notch (42) defines a notch passage (44) between notch passage first and second ends (45)(46) which open on the thread carrier external surface (47). The notch (42) can be disposed angularly across the thread carrier longitudinal axis (48) of the thread carrier (3) to dispose the notch passage first end (45) facing away from the chamber port (20) proximal the thread carrier terminal end (7) and the notch passage second end (46) facing toward the chamber port (20) distal from the thread carrier terminal end (7). The hook (40A) or the pair of hooks (40A)(40B) engage the thread carrier (3) flexing at least one resiliently flexible hook member (39A) or pair of resiliently flexible hook members (39A)(39B) and aligning one of the pair of hooks (40A)(40B) with the notch passage second end (46). Resilient flexure moves the hook (40A) into the notch passage second end (46). The hook (40A) travels through the notch passage (44) and disengages the thread carrier (3) by egress from the notch passage first end (45).

Now referring primarily to FIGS. 17 through 20, the thread carrier (3) can be coupled to the drive member first end (49) and extend axially outward to terminate in a thread carrier terminal end (7). The thread carrier (3) can comprise a slender rod which can, but need not necessarily, taper approaching the thread carrier terminal end (7). The taper can be sufficient to allow the thread carrier (3) to pass through a particular type of substrate (15), and as to particular embodiments, the thread carrier (3) can taper to a sharp point at the thread carrier terminal end (7) to pass through a substrate (15) comprising animal tissue. A thread carrier aperture element (43) can be disposed a distance axially from said thread carrier terminal end (7). The thread carrier aperture element (43) defines a thread carrier aperture (50). As to particular embodiments, the thread carrier aperture (50) can have a thread carrier aperture axis (51) disposed generally orthogonal to the thread carrier longitudinal axis (48) and generally orthogonal to the plane (52) longitudinally bisecting the chamber port (20) (as shown in the cross section of FIG. 18 which longitudinally bisects the chamber port (20) generally orthogonal to the thread carrier aperture axis (51)).

Now referring primarily to FIGS. 1 through 6, embodiments of the suturing apparatus (1) can include a housing (53). The housing (53) can include a handle (54) and a tubular member (11) which outwardly axially extends from the handle (54) terminating in the suturing probe (10). The handle external surface (55) can, but need not necessarily, be configured to be grippingly engaged by the human hand.

Figure 7:
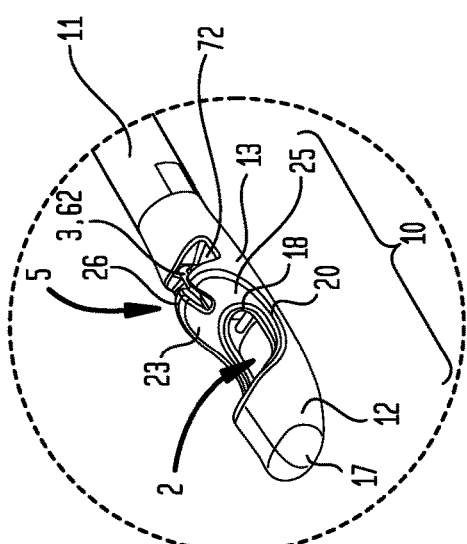
FIG. 7 is an enlarged view of the suturing probe shown in FIG. 1.
Figure 9:
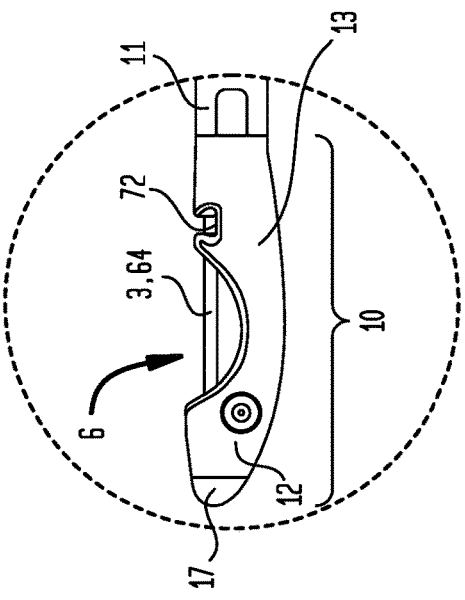
FIG. 9 is an enlarged view of the suturing probe shown in FIG. 3.

Again, referring primarily to FIGS. 17 through 20, the handle (54) can receive in axial sliding engagement a thread carrier driver (56). The thread carrier driver (56) can include an elongate drive member (57) having a length disposed between a drive member first end (49) and a drive member second end (58). The elongate drive member (57) moves axially inside of the handle (54) in response to a drive member actuator (59). As to particular embodiments, a drive member actuator slot (60) can be disposed in the handle (54) and the drive member actuator (59) can be configured to extend through the drive member actuator slot (60) to present a pressible drive member actuator button (61) which upon forcible urging generates corresponding axial movement of the elongate drive member (57) inside of the handle (54). As to particular embodiments, the thread carrier driver (56) can be operated bidirectionally to concurrently reciprocally position the thread carrier terminal end (7) between a thread carrier first position (62) which locates the thread carrier terminal end (7) inside of a second longitudinal channel (63) which opens to the probe external surface (13) outside of the substrate capture chamber (2) and a thread carrier second position (64) with the thread carrier terminal end (7) located in the thread capture chamber (8)(as shown in the examples of FIG. 7 thorough 10). The second longitudinal channel (63) can be fluidically discrete from the first longitudinal channel (36) coupled to the vacuum source (21). Accordingly, the thread carrier (3) disposed and reciprocally moved in the second longitudinal channel (63) from the first position (62) to the second position (64) outside of the substrate capture chamber (2) does not require a seal engaging the thread carrier (3) to maintain reduced chamber pressure (22) in the substrate capture chamber (2) generated in the first longitudinal channel (36) fluidically coupled to the vacuum source (21).

Figure 17:
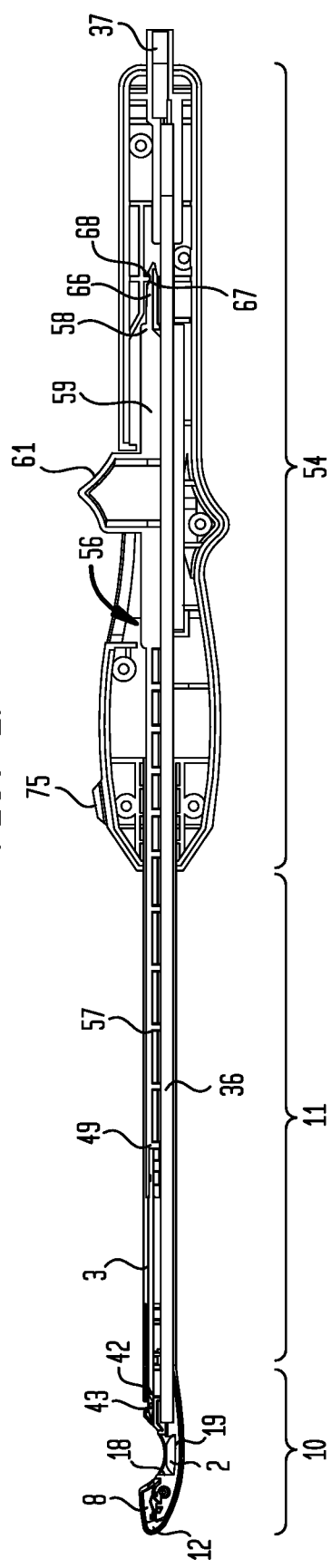
FIG. 17 is a cross section view 17-17 of the particular embodiment of the suturing apparatus shown in FIG. 6.
Figure 18:
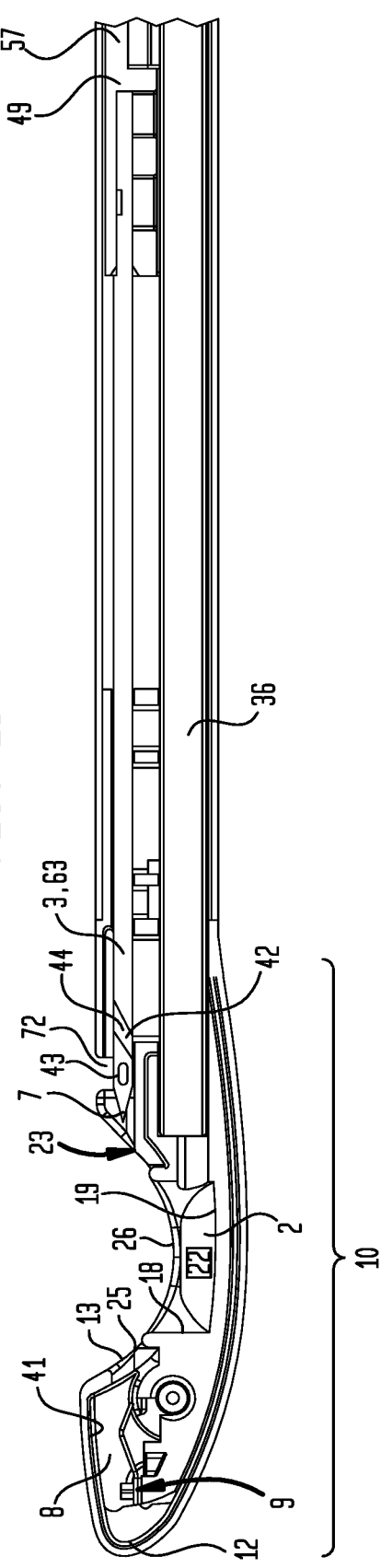
FIG. 18 is an enlarged view of a portion of the cross section of the suturing probe shown in FIG. 17.
Figure 24:
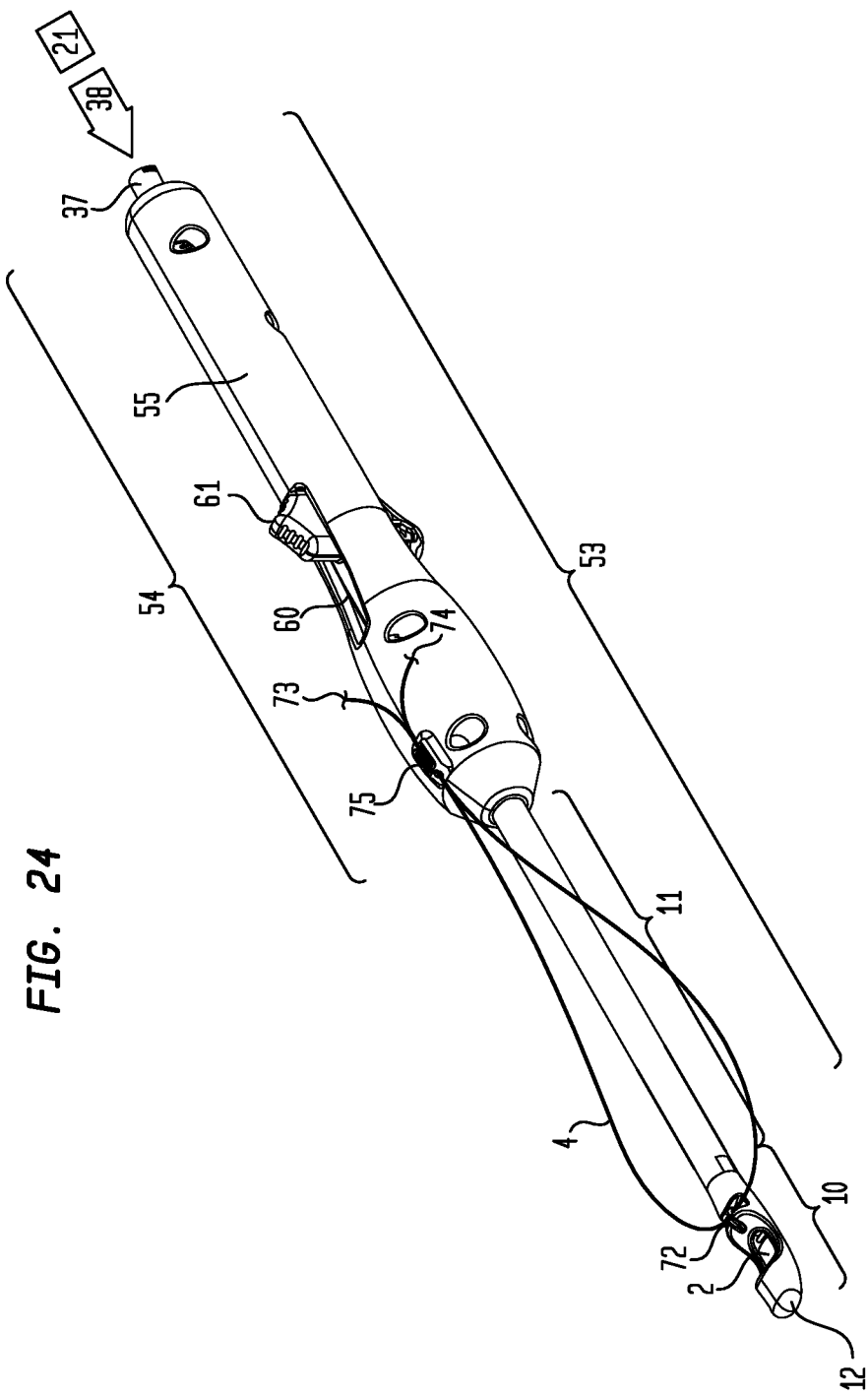
FIG. 24 is a perspective view of a particular embodiment of a suturing apparatus having a thread passing through the thread carrier aperture and disposed in a thread catch.
Figure 25:
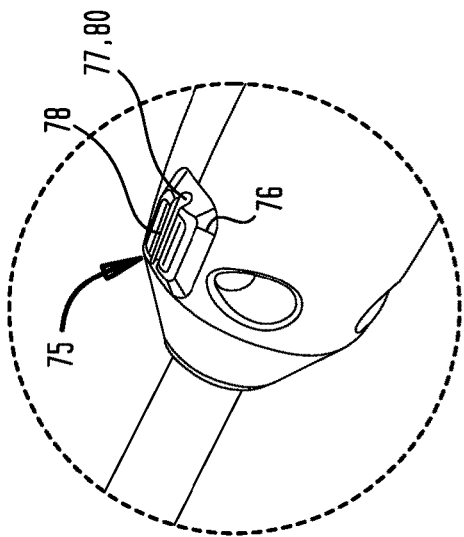
FIG. 25 is an enlarged perspective view of a thread catch as shown in FIG. 1.
Figure 26:
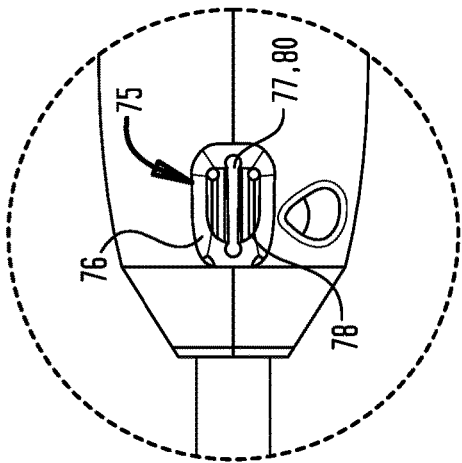
FIG. 26 is an enlarged perspective view of a thread catch as shown in FIG. 1.
Figure 27:
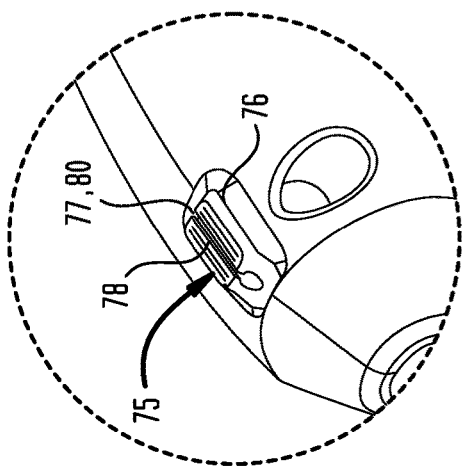
FIG. 27 is an enlarged side view of a particular embodiment of a thread catch.
Figure 28:
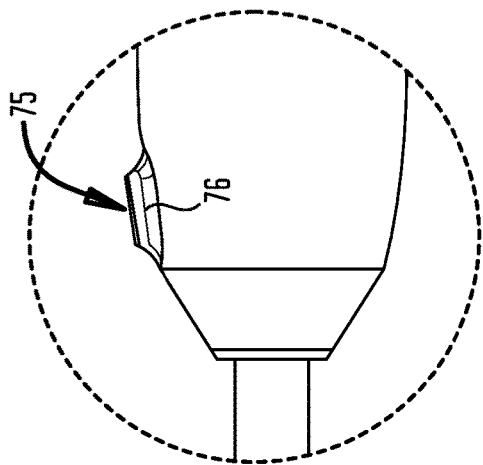
FIG. 28 is an enlarged plan view of a particular embodiment of a thread catch.

Now referring primarily to FIGS. 17 through 19, the housing (53) can be configured to provide a vacuum port (37) opening on the handle external surface (55) (as shown in the examples of FIGS. 1 through 6 and 17 through 19). The vacuum port (37) can be coupled to a vacuum source (21) (as shown in the example of FIGS. 1 and 2). The vacuum source (21) can comprise any of a variety of conventional vacuum or suction pumps. The vacuum source (21) can be operated to generate a reduced chamber pressure (22) in the substrate capture chamber (2).

Now referring primarily to FIGS. 21 through 23, the drive member second end (58) can be coupled to an arrest assembly (65). The arrest assembly (65) can include one or more of an arrest member (66), a prong receiver (67), and a prong (68). The arrest member (66) can have a length disposed between an arrest member first end (69) and an arrest member second end (70). The arrest member first end (69) can be coupled to the thread carrier driver (56). The arrest member second end (70) can have a taper extending toward the arrest member second end (70). Disposed between the arrest member first and second ends (69)(70) can be a prong receiver (67). The prong receiver (67) can engage the prong (68) which can be coupled to the internal surface (71) of the handle (54). The thread carrier driver (56) can be operable to concurrently axially move the thread carrier (3) and the arrest member (66). The arrest member (66) can flex, allowing the prong (68) to disengage the prong receiver (67) when the thread carrier driver (56) operates to move the thread carrier (3) toward the thread carrier second position (64). The arrest member (66) can also flex to allow the prong (68) to traverse along the taper of the arrest member second end (70) toward the prong receiver (67), where the prong (68) can engage the prong receiver (67) when the thread carrier driver (56) operates to move the thread carrier (3) toward the thread carrier first position (62).

Now referring primarily to FIGS. 1 through 11 and 24, a thread (4) can be disposed in the thread carrier aperture element (43). To assist in disposing the thread (4) in the thread carrier aperture element (43), particular embodiments, can include a thread slot (72). The thread slot (72) can be disposed in the suturing probe (10) adjacent the opening of the second longitudinal channel (63) in the suturing probe external surface (13). The location of the thread carrier aperture element (43) disposed in the first position (62) can align with the thread slot (72) to permit a thread (4) to be passed through the thread slot (72) and the thread carrier aperture element (43).

Now referring primarily to FIGS. 24 through 28, in particular embodiments, a method in a suturing apparatus (1) can include passing a first end (73) of a thread (4) through the thread carrier aperture element (43) disposed on the thread carrier (3). In particular embodiments, the method can further include passing the first end (73) of the thread (4) through the thread carrier aperture element (43) while it is aligned with the thread slot (72) disposed in the handle (54). In particular embodiments, the second end (74) of the thread (4) (or both ends of the thread (4)) can be retained in a thread catch (75) disposed on the handle (54). An embodiment of the thread catch (75) can include a thread catch base (76) including a thread catch slot (77) configured to catch and retain a thread (4). In the embodiment, shown in FIGS. 24 through 28, the thread catch (75) can, but need not necessarily include, one or more friction pads (78) disposed in opposed relation about the thread catch slot (77). In particular embodiments, the friction pads (78) can comprise an elastomeric material which increases friction on the thread (4) when disposed in the thread catch slot (77). In particular embodiments, the thread catch (75) can include a thread catch base (76) including a thread catch aperture element (80). The thread catch aperture element (80) can define a thread catch aperture communicating between a distal end of the thread catch (75) and a proximal end of the thread catch (75). The thread (4) can be passed through the thread catch aperture in a distal to proximal direction.

Referring primarily to FIGS. 29 through 32, a method in a suturing apparatus (1) can include driving a thread carrier (3) slidingly engaged to the suturing probe (10) toward the thread capture chamber (8). Slidingly engaging a thread capture assembly (9) disposed in the thread capture chamber (8) with the thread carrier (3) carrying the thread (4).

Figure 29:
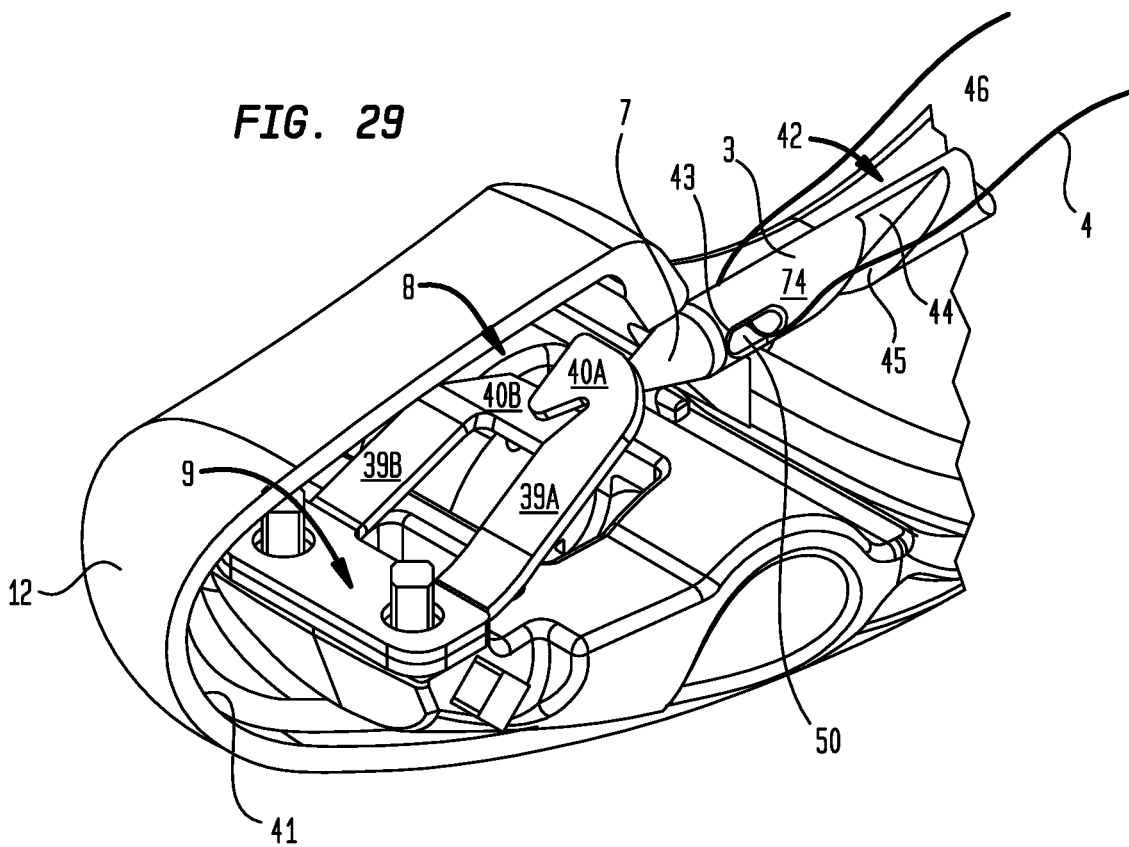
FIG. 29 is an enlarged view of a particular embodiment of a thread carrier and a thread capture chamber showing the position of thread carrier extended a distance into the thread capture chamber.
Figure 30:
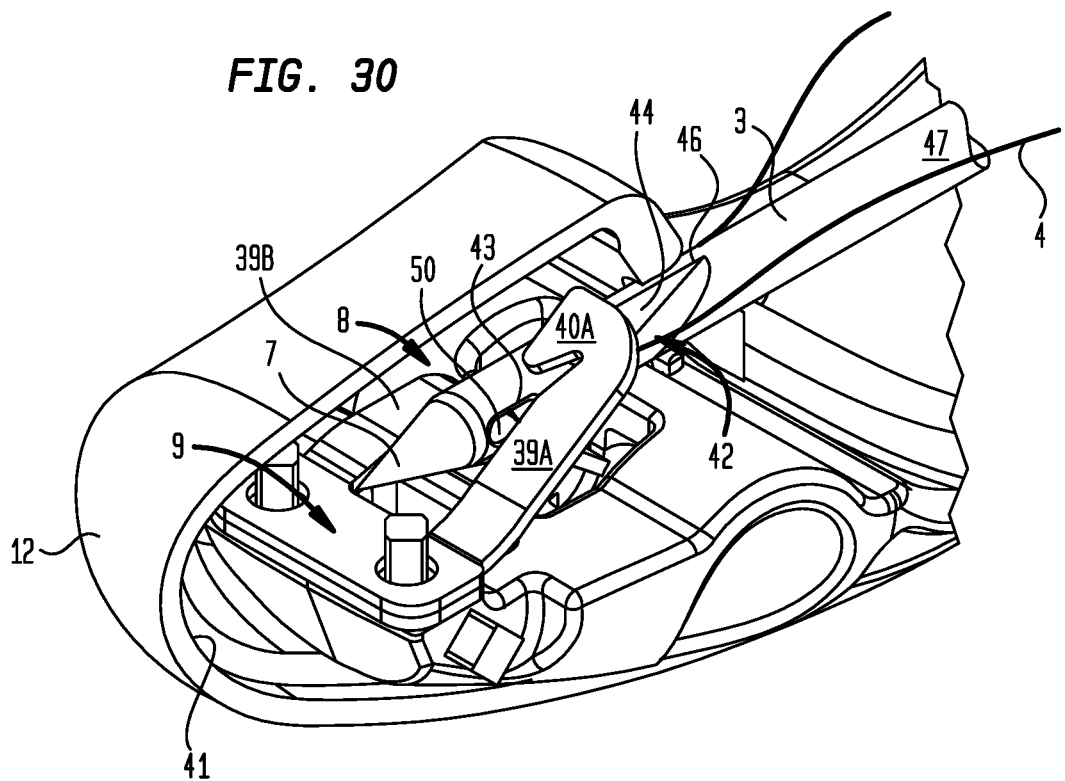
FIG. 30 is an enlarged view of a particular embodiment of a thread carrier and a thread capture chamber showing the position of the thread carrier extended a distance into the thread capture chamber to slidingly engage a thread capture assembly.
Figure 31:
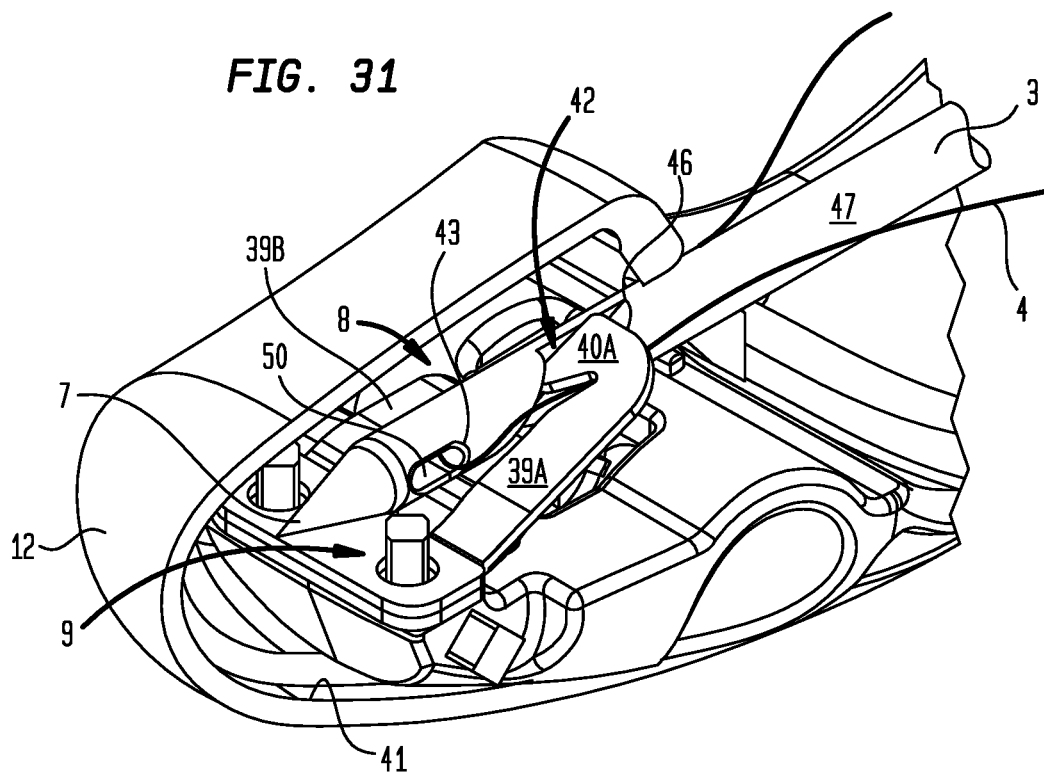
FIG. 31 is an enlarged view of a particular embodiment of a thread carrier and a thread capture chamber showing the position of the thread carrier extended a distance into the thread capture chamber to align a hook of the thread capture assembly with a notch in the thread carrier.
Figure 32:
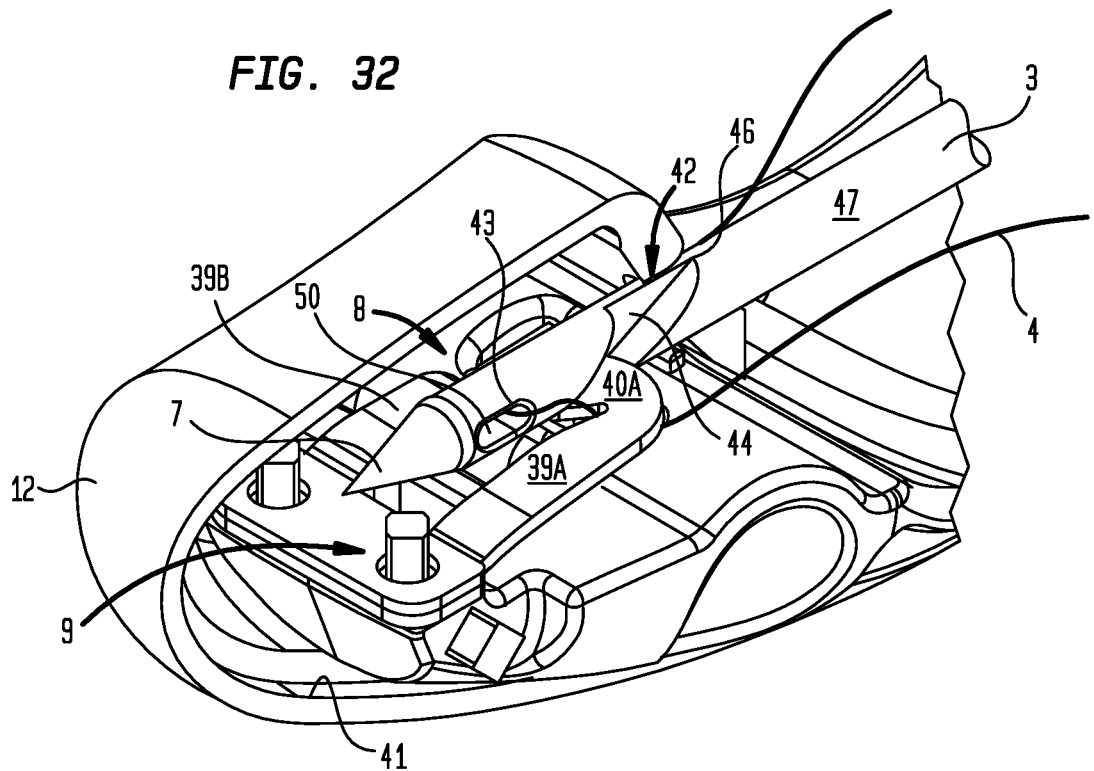
FIG. 32 is an enlarged view of a particular embodiment of a thread carrier and a thread capture chamber showing the thread carrier being withdrawn from the thread capture chamber allowing the hook of the thread capture assembly to pass through the notch to capture the thread on thread capture assembly.

Disposing the thread (4) adjacent at least one resiliently flexible hook member (39A) terminating in a hook (40A). Aligning the hook (40A) with a notch second end (46) of the notch (42) disposed in the thread carrier (3) (as shown in the examples of FIGS. 29 and 30). Driving the thread carrier (3) slidingly engaged to the suturing probe (10) away from the thread capture chamber (8) to move the hook (40A) through the notch passage (44). Capturing the thread (4) on the hook (40A) (as shown in the example of FIGS. 31 and 32).

Figure 33C:
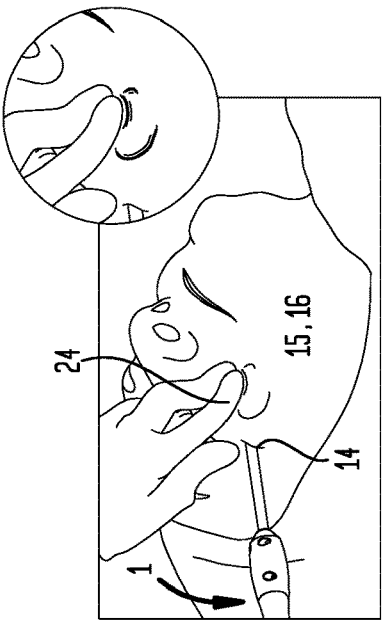
FIG. 33C is a depiction of a particular method of palpating a substrate toward a substrate capture chamber of the suturing apparatus.
Figure 33B:
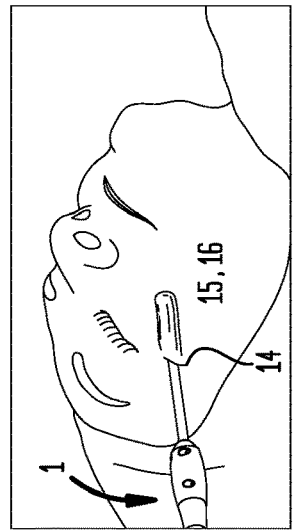
FIG. 33B is a depiction of a particular method of inserting a suturing probe in a body opening.
Figure 33A:
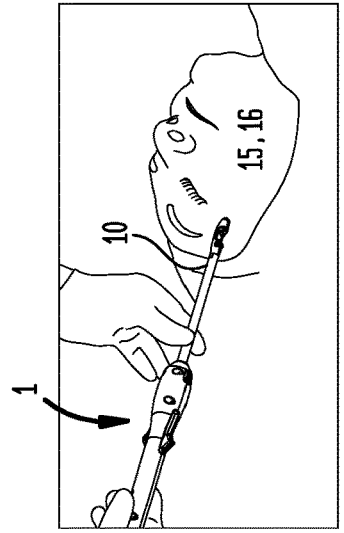
FIG. 33A is a depiction of a particular method of using an embodiment of a suturing apparatus.
Figure 33E:
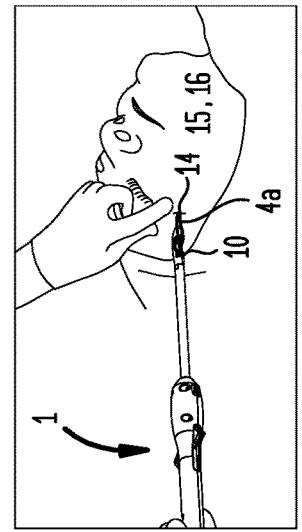
FIG. 33E is a depiction of a particular method of disposing a suture loop in the substrate and removing a suturing probe from a body opening.
Figure 33D:
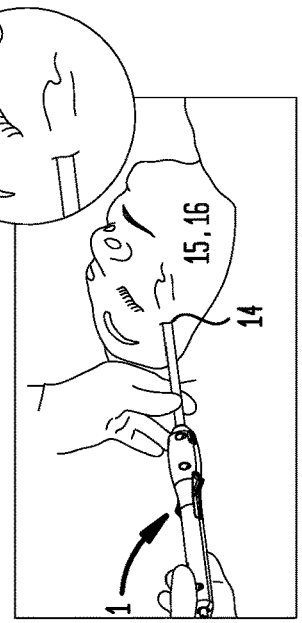
FIG. 33D is a depiction of a particular method of operating the suturing apparatus to drive the thread carrier through a substrate.

Now referring primarily to FIG. 33A through 33E, a method in a suturing apparatus (1) can include passing a first end (73) of a thread (4) through the thread carrier aperture element (43) disposed on the thread carrier (3) (as shown in the example of FIG. 33A). Inserting a suturing probe (10) into a body opening (14) of a substrate (15) (as shown in the example of FIG. 33 B). Forcibly urging the substrate (15) toward a substrate capture chamber (2) disposed in the suturing probe (10) which as to particular embodiments, includes contacting the substrate (15) with a finger (24) or other instrument or device (as shown in the example of FIG. 33C). Capturing the substrate (15) in the substrate capture chamber (2), which can, but need not necessarily, include generating a reduced chamber pressure (22) in the substrate capture chamber (2) by operation of a vacuum source (21) to draw and retain an amount of the substrate (15) in the substrate capture chamber (2). Driving a thread carrier (3) slidably engaged in the suturing probe (10) toward a thread capture chamber (8). Passing the thread carrier (3) carrying the thread (4) through the substrate (15) outside of the substrate capture chamber (2) into the thread capture chamber (8) (as shown in the example of FIG. 33D). Engaging the thread carrier (3) with a thread capture assembly (9) disposed in the thread capture chamber (8). Capturing the thread (4) on the thread capture assembly (9). Reciprocally driving a thread carrier (3) from the thread capture chamber (8) and through the substrate (15) to generate a thread loop (4a) in the substrate (15) (as shown in the example of FIG. 33E and FIG. 34). In particular embodiments, the methods can further include inserting a substrate capture chamber insert (31) into the substrate capture chamber (2).

With regards to driving a thread carrier (3) in the suturing probe (10) toward a thread capture chamber (8), the method can further include pressing a drive member actuator button (61) extending through the drive member actuator slot (60) in a handle (54) of the suturing apparatus (1). The pressing can generate movement in the thread carrier (3) in a first direction (79) toward the thread capture chamber (8). The movement of the thread carrier (3) in a first direction (79) can pass the thread carrier (3) through the substrate (15) outside of the substrate capture chamber (2) into the thread capture chamber (8) without compromising the integrity of the reduced chamber pressure (22) generated by a vacuum source (21) fluidically coupled to the substrate capture chamber (2). In particular embodiments, the method can further include flexing an arrest assembly (65), thereby disengaging the prong (68) from the prong receiver (67) and advancing the prong (68) along the taper of the arrest member second end (70) and to permit the movement of the thread carrier (3) in the first direction (79).

Now referring primarily to FIG. 34, there can be an advantage in varying the configuration or volume of the substrate capture chamber (2). Various configurations and volumes of the substrate capture chamber (2) can occur by utilizing a substrate capture chamber insert (31) and the option of utilizing a vacuum source (21) to reduce pressure (22) in the substrate capture chamber (2) to correspondingly vary the suture purchase (30) in the substrate (15, 16) depending on the requirements of the application. In particular embodiments which include a vacuum source (21), reducing pressure (22) in the substrate capture chamber (2) can capture an increased amount of substrate (15) in the substrate capture chamber (2), thereby increasing the suture purchase (30). The suture purchase (30) can be adjusted by the use of a substrate capture chamber insert (31) which varies the volume of the substrate capture chamber (2) available to receive the substrate (15). In other particular embodiments, a substrate capture chamber insert (31) can be utilized without a vacuum source (21), decreasing the suture purchase (30) as opposed to an application which utilizes a vacuum source (21). Thus, by altering the factors of utilizing a substrate capture chamber insert (31) and the utilization of a vacuum source (21), the suture purchase (30) can be increased or decreased depending upon the application.

Now referring to FIGS. 34 and 35 through 43, particular embodiments of the suturing apparatus (1) can further include a substrate reinforcing element (80) which can, by operation of the suturing apparatus (1), be disposed under the thread (4)(as shown in the example of FIG. 34) to provide mechanical support to the suture purchase (30) in the substrate (15)(tissue (16)) to prohibit or reduce the possibility of the thread (4) tearing through the substrate (15)(tissue (16)) by diffusing suturing forces over a greater substrate area (83) (shown in the example of FIG. 34 in broken line) than contacted by the thread (4)(suture) alone. The substrate reinforcing element (80) can, but need not necessarily, protect the substrate area (83) or deliver compositions to the substrate area (83) such as drugs, antibiotics, hormones, or the like, or combinations thereof. The substrate reinforcing element (80) can be produced from a wide variety of solid, porous, woven, or apertured non-woven substrate reinforcing materials, including or consisting of: polytetrafluoroethylene, polypropylene, polyethylene, polyethersulfone, polyurethane, and felt, or combinations thereof.

In particular embodiments, the substrate reinforcing element (80) can be produced from a biodegradable material. "Biodegradable" for the purposes of this invention means the ability of any biocompatible material to breakdown within the physiological environment of the substrate area (83) by one or more physical, chemical, or cellular processes at a rate consistent with providing structural reinforcement of the substrate area (83) or delivering pharmaceuticals at a therapeutic level controllable by selection of a polymer or mixture of polymers (also referred to as polymeric materials), including, but not limited to: poly-4-hydroxybutyrate (P4HB), polylactide polymers (PLA), copolymers of lactic and glycolic acids (PLGA), polylactic acid-polyethylene oxide copolymers, poly(ε-caprolactone-co-L-lactic acid (PCL-LA), glycine/PLA copolymers, PLA copolymers involving polyethylene oxides (PEO), acetylated polyvinyl alcohol (PVA)/polycaprolactone copolymers, hydroxybutyrate-hydroxyvalerate copolymers, polyesters such as, but not limited to, aspartic acid and different aliphatic diols, poly(alkylene tartrates) and their copolymers with polyurethanes, polyglutamates with various ester contents and with chemically or enzymatically degradable bonds, other biodegradable nonpeptidic polyamides, amino acid polymers, polyanhydride drug carriers such as, but not limited to, poly(sebacic acid) (PSA), aliphatic-aromatic homopolymers, and poly(anhydride-co-imides), poly(phosphoesters) by matrix or pendant delivery systems, poly(phosphazenes), poly(iminocarbonate), crosslinked poly(ortho ester), hydroxylated polyester-urethanes, or the like.

Figure 38:
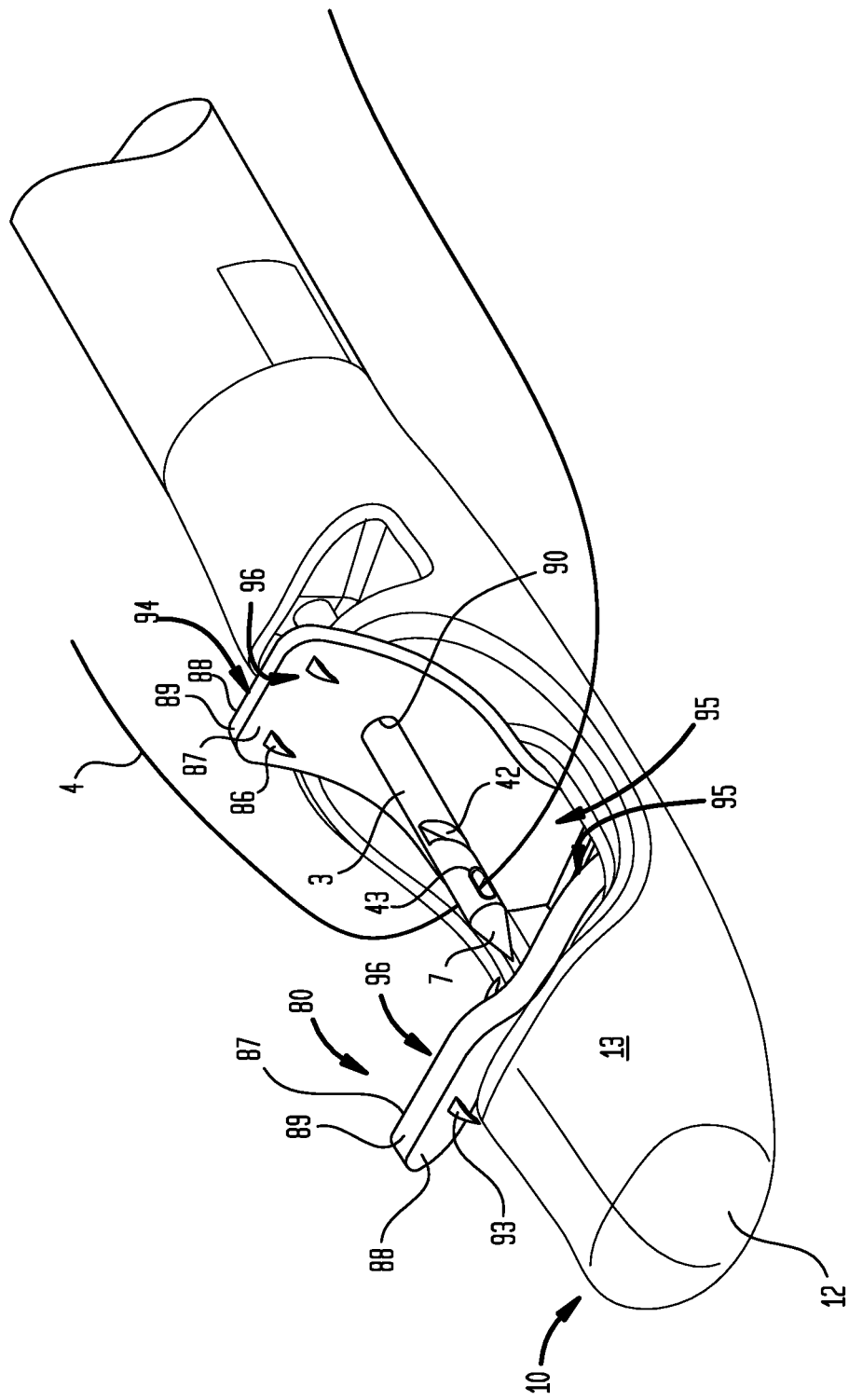
FIG. 38 is a perspective view of an embodiment of a suturing apparatus including another particular embodiment of a substrate reinforcing element.

Now referring generally to FIGS. 35 through 43, embodiments of the substrate reinforcing element (80) can include a body (84) capable of being penetrated by the thread carrier (3) when the thread carrier (3) moves in a first direction (79)(as shown in the examples of FIGS. 36, 39 and 42) toward the thread capture chamber (8) and of releasing the thread carrier (3) when the thread carrier (3) moves in a second direction (85) away from the thread capture chamber (8) while retaining the thread (4). In further particular embodiments, one or more retaining elements (86) can be coupled to the substrate reinforcing element (80)(as shown in the example of FIG. 38). Each of the one or more retaining elements (86) can increase the adherence of the substrate reinforcing element (80) to the substrate (15). Examples of a retaining element (86) can include barbs, projections, hooks, prongs, bristles, spikes, points, spines, or other features the increase adherence of the substrate reinforcing element (80) to the substrate (15)(16).

Figure 35:
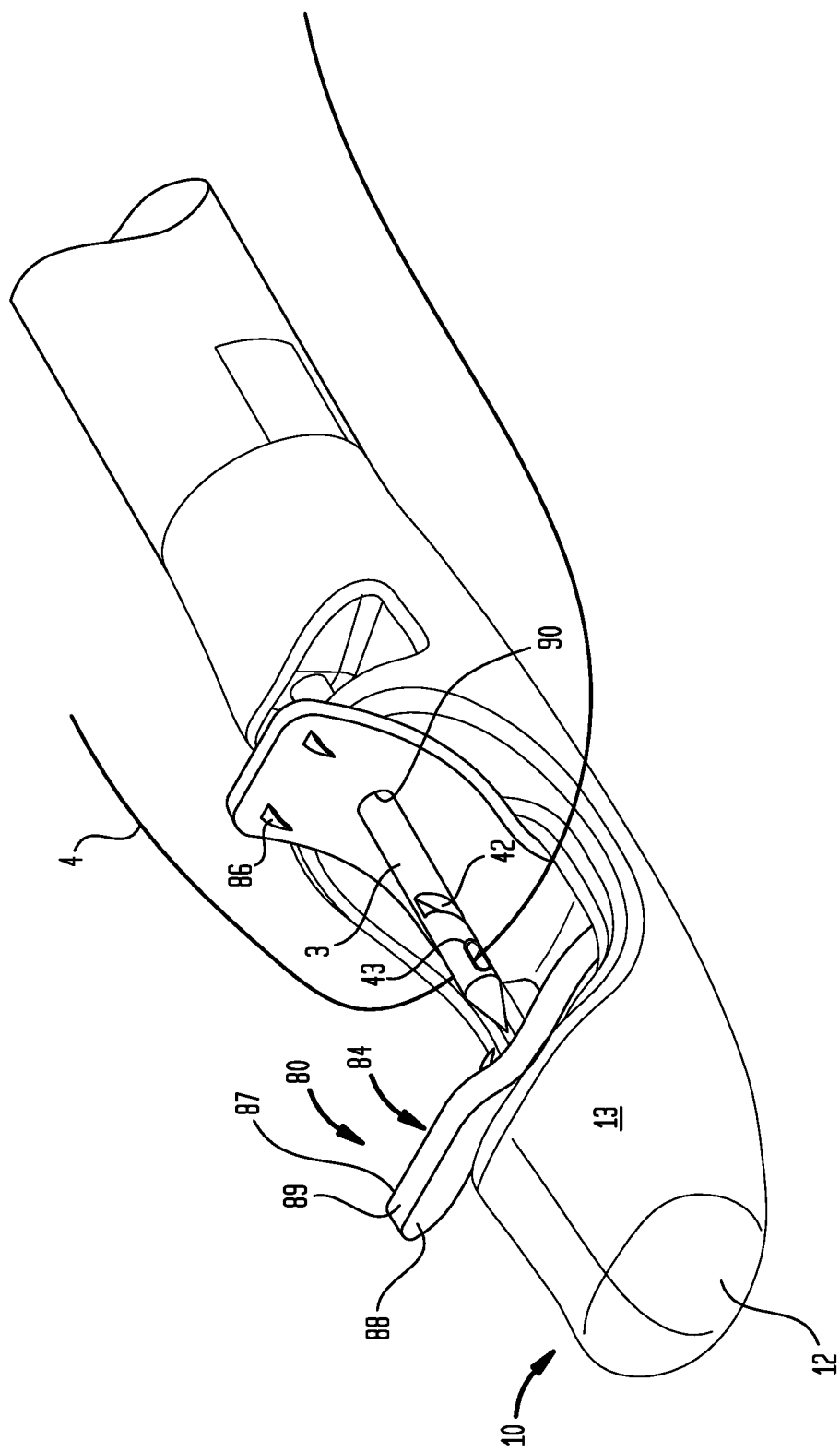
FIG. 35 is a perspective view of an embodiment of a suturing apparatus including a particular embodiment of a substrate reinforcing element.

Now referring primarily to FIG. 35 through 37, in particular embodiments, the substrate reinforcing element (80) can include a one-piece body (84) disposable in the substrate capture chamber (2) of the suturing apparatus (1). The one-piece body (84) can be formed as or cut from a flexible sheet material have a thickness disposed between a top surface (87) and a bottom surface (88). The top surface (87) and the bottom surface (88) can each extend to a peripheral edge (89). The peripheral edge (89) can define a rectangle, square, circle, elongate strip, or other configuration compatible with the substrate suturing application. In particular embodiments, the body (84) can be bowed or folded within the substrate capture chamber (2) of the suturing apparatus (1)(as shown in the example of FIGS. 36 and 37). The substrate (15) which can, but need not necessarily, be a tissue (16), can be captured within the bowed or folded body (84) of the substrate reinforcing element (80)(as shown in the illustrative example of FIG. 36). The thread carrier (3) can penetrate the one-piece body (84) at a first and second puncture points (90)(91) when it moves in a first direction (79) toward the thread capture chamber (8). The thread capture assembly (9) can capture the thread (4) as above described. The thread carrier (3) can move in a second direction (85) away from the thread capture chamber (8) egressing through the first and second puncture points (90)(91) to release the thread carrier (3) with the thread (4) retained within the first and second puncture points (90)(91) in the one-piece body (84) of the substrate reinforcing element (80) and the substrate (15)(16) (as shown in the example of FIG. 34).

Again, referring primarily to FIGS. 41 through 43, in particular embodiments, the body (84) can, but need not necessarily, further include one or more aperture elements (92) whether pre-formed in the body (84) or formed by the penetration of thread carrier (3) through the thickness of the body (84) a first and second puncture points (90)(91). Pre-formed aperture elements (92) can be located on the body (84) bowed or folded within the substrate capture chamber (2) of the suturing apparatus (1) to receive the thread carrier (4) when it moves in a first direction (79) toward the thread capture chamber (8). The pre-formed aperture elements (92) can be circular apertures or elongate slots or slits which facilitate movement of the body (84) in relation to the thread carrier (4) toward the central area of the aperture element (92).

Now referring primarily to FIGS. 38 through 40, in particular embodiments, the substrate reinforcing element (80) can include a pair of leaves (93)(94) each having a length between leave first and second ends (95)(96). The leaf first ends (95) can be secured within the substrate capture chamber (2) by leaf retaining elements (82) with the leaf second ends (96) disposed a distance apart outside of the substrate capture chamber (2). The leaf retaining elements (82) can each comprise a recess disposed in the bottom of the substrate capture chamber (2). The recess having recess sidewalls positioned to correspondingly receive and grip the leaf first ends (95) during normal operation of the suturing apparatus (1). The leaf retaining elements (82) can also take the form of flexibly resilient members which outwardly flex to receive and grip the leaf first ends (95). The substrate (15)(16) can be captured between the pair of leaves (93)(94) of the substrate reinforcing element (80) within the substrate capture chamber (2). The thread carrier (3) can penetrate the pair of leaves (93)(94) at a first and second puncture points (90)(91) when it moves in a first direction (79) toward the thread capture chamber (8). The thread capture assembly (9) can capture the thread (4) as above described. The thread carrier (3) can move in a second direction (85) away from the thread capture chamber (8) egressing through the first and second puncture points (90)(91) to release the thread carrier (3) with the thread (4) retained within the first and second puncture points (90)(91) in the body (84) of the substrate reinforcing element (80). One or both of the pair of leaves (93)(94) can include an aperture element (92) as above described.

Now referring primarily to FIGS. 41 through 43, in particular embodiments, the substrate reinforcing element (80) can comprise a tubular member (97) having a length disposed between a tubular member first end (98) and a tubular member second end (99). The tubular member (97) can be disposed on or about the thread carrier (3) whereby movement of the thread carrier (3) correspondingly generates movement of the tubular member (97). In particular embodiments, the thread carrier (4) can pass longitudinally through the substrate reinforcing element (80) to generate a tubular member (97) having an interior passage (100). In particular embodiments, the tubular member (97) can, but need not necessarily, have a preformed interior passage (100) extending between the tubular member first end (98) and the tubular member second end (99). The interior passage (100) can be formed to provide an interior diameter (101) which receives the thread carrier (3) when the thread carrier (3) moves in a first direction (79) toward the thread capture chamber (8). The tubular member (97) can move with the thread carrier (3) in a first direction (79) to be disposed within the substrate (15) as the thread carrier (3) passes into the thread capture chamber (8). The interior passage (100) can release the thread carrier (3) when the thread carrier (3) moves in a second direction (85) away from the thread capture chamber (8) to locate the tubular member (97) within the substrate (15)(16) with the thread (4) disposed in the interior passage (100).

Again, referring primarily to FIGS. 41 through 43, in particular embodiments, a first flange (103) can extend radially outward from the tubular member (97) proximate the tubular member first end (98). In particular embodiments, a second flange (104) can extend radially outward from the tubular member (97) proximate the tubular member second end (99). Each of the first and second flanges (103)(104) can comprise annular flanges which extend the interior passage (100) to communicate with first and second flange ends (105)(106).

In particular embodiments, the first or second flange (103)(104) can be configured as a cone (107) or truncated cone (108) with the apex of the cone (107) or the lesser diameter end (109) of the truncated cone disposable proximate the thread capture chamber (8) and the greater diameter end (110) of the truncated cone (108) distal the thread capture chamber (8); however these illustrative examples are not intended to obviate first and second flanges (103)(104) configured generally as a sphere, an ovoid, a cylinder, an inverted truncated cone, or any configuration which radial extends outward of the tubular member (97) to oppose being released from the substrate (15) upon movement of the thread carrier (3) in the second direction (85).

Again referring to FIGS. 35 through 37, in particular embodiments, the tubular member (97) can shorten and correspondingly radially expand in response to longitudinal compressing forces applied as the thread carrier (3) enters the thread capture chamber (8) and the greater diameter tubular member first end (98) correspondingly contacts the suturing probe external surface (13) with the tubular member second end (99) further driven toward the thread capture chamber (8) by an abutting element (111) disposed on the thread carrier (3). As an illustrative example, the tubular member (97) can include a plurality of radially expandable cylindrical elements (112) which are relatively independent in their ability to expand and to flex relative to one another in a manner associated with expandable stents; however, this illustrative example is not intended to obviate embodiments in which the tubular member (97) radially expands by deformation of a compressible material included in the tubular member (97).

In particular embodiments of the suturing apparatus (1) including a substrate reinforcing element (80), as described above, a method can include disposing the substrate reinforcing element (80) (whether as a one piece body (84) or as a pair of leaves (93)(94)) within or adjacent the substrate capture chamber (2), capturing a substrate (15) in the substrate capturing chamber (2), and driving the thread carrier (3) carrying a thread (4) toward the thread capture chamber (8) whereby the thread carrier (3) carrying the thread (4) passes through the substrate reinforcing element (80) and the substrate (15) outside of the substrate capture chamber (2). The method can further include capturing the thread (4) on a thread capture assembly (9) within the thread capture chamber (8) and withdrawing the thread carrier (3) through the substrate reinforcing element (80) and the substrate (15) to dispose the substrate reinforcing element (80) adjacent the substrate (15) with the thread (4) passing through the substrate reinforcing element (80) and the substrate (15) outside of the substrate capture chamber (2).

In particular embodiments of a substrate reinforcing element (80) including a tubular member (97), a method can include disposing the substrate reinforcing element (80) adjacent the substrate capture chamber (2) having a tubular member first end (98) or tubular member second end (99) adjacent the thread carrier terminal end (7). The method can further include passing the thread carrier (3) through the tubular member (97) between tubular member first and second ends (98)(99) to generate an interior passage (100). In particular embodiments in which the interior passage (100) may be pre-formed, the method can include passing the thread carrier (3) through the interior passage (100). The method can further include moving the tubular member (97) by operation of the thread carrier (3) in a first direction (79) toward the thread capture member (8). The method can further include passing the tubular member (97) through the substrate (15) concurrent with passing the thread carrier (3) into the thread capture assembly (9). The method can further include capturing the thread (4) on a thread capture assembly (8) within the thread capture chamber (8) and withdrawing the thread carrier (3) through the substrate reinforcing element (80) and the substrate (15) to dispose the substrate reinforcing element within the substrate (15) with the thread (4) passing through the substrate reinforcing element (80) and the substrate (15) outside of the substrate capture chamber (2).

In particular embodiments of a substrate reinforcing element (80) including a one-piece body (84), the one-piece body (84) can be wholly or partially disposed in the substrate capture chamber (2) prior to or after capturing a substrate (15) in the substrate capture chamber (2).

As can be easily understood from the foregoing, the basic concepts of the present invention may be embodied in a variety of ways. The invention involves numerous and varied embodiments of a mountable carrier and methods for making and using such mountable carrier including the best mode.

As such, the particular embodiments or elements of the invention disclosed by the description or shown in the figures or tables accompanying this application are not intended to be limiting, but rather exemplary of the numerous and varied embodiments generically encompassed by the invention or equivalents encompassed with respect to any particular element thereof. In addition, the specific description of a single embodiment or element of the invention may not explicitly describe all embodiments or elements possible; many alternatives are implicitly disclosed by the description and figures.

It should be understood that each element of an apparatus or each step of a method may be described by an apparatus term or method term. Such terms can be substituted where desired to make explicit the implicitly broad coverage to which this invention is entitled. As but one example, it should be understood that all steps of a method may be disclosed as an action, a means for taking that action, or as an element which causes that action. Similarly, each element of an apparatus may be disclosed as the physical element or the action which that physical element facilitates. As but one example, the disclosure of a "suture" should be understood to encompass disclosure of the act of "suturing"—whether explicitly discussed or not—and, conversely, were there effectively disclosure of the act of "suturing", such a disclosure should be understood to encompass disclosure of a "suture" and even a "means for suturing." Such alternative terms for each element or step are to be understood to be explicitly included in the description.

In addition, as to each term used it should be understood that unless its utilization in this application is inconsistent with such interpretation, common dictionary definitions should be understood to be included in the description for each term as contained in the Random House Webster's Unabridged Dictionary, second edition, each definition hereby incorporated by reference.

All numeric values herein are assumed to be modified by the term "about", whether or not explicitly indicated. For the purposes of the present invention, ranges may be expressed as from "about" one particular value to "about" another particular value. When such a range is expressed, another embodiment includes from the one particular value to the other particular value. The recitation of numerical ranges by endpoints includes all the numeric values subsumed within that range. A numerical range of one to five includes for example the numeric values 1, 1.5, 2, 2.75, 3, 3.80, 4, 5, and so forth. It will be further understood that the endpoints of each of the ranges are significant both in relation to the other endpoint, and independently of the other endpoint. When a value is expressed as an approximation by use of the antecedent "about," it will be understood that the particular value forms another embodiment. The term "about" generally refers to a range of numeric values that one of skill in the art would consider equivalent to the recited numeric value or having the same function or result. Similarly, the antecedent "substantially" means largely, but not wholly, the same form, manner or degree and the particular element will have a range of configurations as a person of ordinary skill in the art would consider as having the same function or result. When a particular element is expressed as an approximation by use of the antecedent "substantially," it will be understood that the particular element forms another embodiment.

Moreover, for the purposes of the present invention, the term "a" or "an" entity refers to one or more of that entity unless otherwise limited. As such, the terms "a" or "an", "one or more" and "at least one" can be used interchangeably herein.

Thus, the applicant(s) should be understood to claim at least: i) each of the suturing systems or substrate reinforcing elements herein disclosed and described, ii) the related methods disclosed and described, iii) similar, equivalent, and even implicit variations of each of these devices and methods, iv) those alternative embodiments which accomplish each of the functions shown, disclosed, or described, v) those alternative designs and methods which accomplish each of the functions shown as are implicit to accomplish that which is disclosed and described, vi) each feature, component, and step shown as separate and independent inventions, vii) the applications enhanced by the various systems or components disclosed, viii) the resulting products produced by such systems or components, ix) methods and apparatuses substantially as described hereinbefore and with reference to any of the accompanying examples, x) the various combinations and permutations of each of the previous elements disclosed.

The background section of this patent application provides a statement of the field of endeavor to which the invention pertains. This section may also incorporate or contain paraphrasing of certain United States patents, patent applications, publications, or subject matter of the claimed invention useful in relating information, problems, or concerns about the state of technology to which the invention is drawn toward. It is not intended that any United States patent, patent application, publication, statement or other information cited or incorporated herein be interpreted, construed or deemed to be admitted as prior art with respect to the invention.

The claims set forth in this specification, if any, are hereby incorporated by reference as part of this description of the invention, and the applicant expressly reserves the right to use all of or a portion of such incorporated content of such claims as additional description to support any of or all of the claims or any element or component thereof, and the applicant further expressly reserves the right to move any portion of or all of the incorporated content of such claims or any element or component thereof from the description into the claims or vice-versa as necessary to define the matter for which protection is sought by this application or by any subsequent application or continuation, division, or continuation-in-part application thereof, or to obtain any benefit of, reduction in fees pursuant to, or to comply with the patent laws, rules, or regulations of any country or treaty, and such content incorporated by reference shall survive during the entire pendency of this application including any subsequent continuation, division, or continuation-in-part application thereof or any reissue or extension thereon.

Additionally, the claims set forth in this specification, if any, are further intended to describe the metes and bounds of a limited number of the preferred embodiments of the invention and are not to be construed as the broadest embodiment of the invention or a complete listing of embodiments of the invention that may be claimed. The applicant does not waive any right to develop further claims based upon the description set forth above as a part of any continuation, division, or continuation-in-part, or similar application.

I claim:

1. A suturing system, comprising:
   a suturing probe including a thread capture chamber disposed adjacent a recessed portion and a substrate capture chamber, said substrate capture chamber having a chamber port open to said recessed portion;
   a thread carrier slidingly engaged to said suturing probe to reciprocally travel within said recessed portion of the suturing probe and outside of said substrate capture chamber to engage and disengage a thread capture assembly disposed in said thread capture chamber, said thread carrier carrying a thread driven in a first direction through a substrate reinforcing element to engage said thread capture assembly which captures said thread, said thread carrier driven in a second direction to disengage said thread capture assembly and withdraw from said substrate reinforcing element; and
   a thread loop disposed in said substrate reinforcing element;
   wherein said substrate reinforcing element includes a pair of leaves of flexible sheet material each having a thickness disposed between a top surface and a bottom surface, each of said top surface and said bottom surface extending to a peripheral edge, said pair of leaves secured a distance apart within said substrate capture chamber with a portion of said pair of leaves disposed outside of said substrate capture chamber, said thread carrier carrying said thread driven in a first direction through said portion of said pair of leaves disposed outside of said substrate capture chamber.

2. The apparatus of claim 1, wherein said substrate reinforcing element comprises a material selected from the group consisting of: polytetrafluoroethylene, polypropylene, polyethylene, polyethersulfone, and polyurethane, and combinations thereof.

3. The apparatus of claim 1, further comprising a leaf retaining element disposed in said substrate capture chamber, said leaf retaining element adapted to retain said pair of leaves.

* * * * *